(12) United States Patent
Panescu et al.

(10) Patent No.: US 12,201,344 B2
(45) Date of Patent: Jan. 21, 2025

(54) SYSTEMS AND METHODS FOR PULSED-FIELD ABLATION WITH CHARGE-BALANCED WAVEFORMS

(71) Applicant: CRC EP, INC., Lake Oswego, OR (US)

(72) Inventors: Dorin Panescu, San Jose, CA (US); Tho Nguyen, Huntington Beach, CA (US); Henning Ebert, Berlin (DE); Steffen Holzinger, Berlin (DE); Sven Bode, Berlin (DE)

(73) Assignee: CRC EP, INC., Lake Oswego, OR (US)

( * ) Notice: Subject to any disclaimer, the term of this patent is extended or adjusted under 35 U.S.C. 154(b) by 0 days.

(21) Appl. No.: 18/604,179

(22) Filed: Mar. 13, 2024

(65) Prior Publication Data
US 2024/0216039 A1 Jul. 4, 2024

Related U.S. Application Data

(63) Continuation of application No. PCT/US2023/012201, filed on Feb. 2, 2023.
(Continued)

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1492* (2013.01); *A61B 34/25* (2016.02);
(Continued)

(58) Field of Classification Search
CPC .......... A61B 2018/00577; A61B 2018/00613; A61B 2018/00767; A61B 2018/00827;
(Continued)

(56) References Cited

U.S. PATENT DOCUMENTS 5,871,505 A * 2/1999 Adams ................. A61N 1/3956
607/5
7,117,034 B2 10/2006 Kronberg
(Continued)

OTHER PUBLICATIONS

International Search Report and Written Opinion mailed Apr. 14, 2023 in PCT/US2023/012201, 9 pages.

*Primary Examiner* — Michael F Peffley
*Assistant Examiner* — Samantha M Good
(74) *Attorney, Agent, or Firm* — Procopio, Cory, Hargreaves & Savitch LLP

(57) ABSTRACT

The present invention relates to a generator (G) for a substantially charge-balanced pulse for application onto at least one electrode pair (101) of a medical device, the generator comprising: a pulse-shaping output stage (POS) for coupling to the at least one electrode pair; an internal pulse generator for applying an internal pulse to the pulse-shaping output stage; wherein the pulse-shaping output stage comprises a transformer (T) and/or a capacitor system (CS) comprising at least one capacitor such that the internal pulse is transformed into a substantially charge-balanced pulse in the at least one electrode pair (I1) when coupled to the pulse-shaping output stage (POS). Further aspects relate to a catheter, a system, a method.

30 Claims, 11 Drawing Sheets

Related U.S. Application Data

(60) Provisional application No. 63/306,162, filed on Feb. 3, 2022.

(51) Int. Cl.
*A61B 34/00* (2016.01)
*A61B 18/00* (2006.01)

(52) U.S. Cl.
CPC ............... *A61B 2018/00577* (2013.01); *A61B 2018/00613* (2013.01); *A61B 2018/00767* (2013.01); *A61B 2018/00827* (2013.01); *A61B 2018/00875* (2013.01); *A61B 2018/00892* (2013.01); *A61B 2018/126* (2013.01); *A61B 2018/1286* (2013.01)

(58) Field of Classification Search
CPC ........... A61B 2018/00875; A61B 2018/00892; A61B 2018/126; A61B 2018/1286; A61B 18/1206; A61B 18/1492; A61B 34/25
See application file for complete search history.

(56) References Cited

U.S. PATENT DOCUMENTS

| | | | |
|---|---|---|---|
| 2006/0173493 A1 | 8/2006 | Armstrong et al. | |
| 2013/0282079 A1* | 10/2013 | Kallmyer ........... | A61N 1/36125 607/62 |
| 2020/0289185 A1* | 9/2020 | Forsyth .............. | A61B 18/1477 |

* cited by examiner

SYSTEMS AND METHODS FOR PULSED-FIELD ABLATION WITH CHARGE-BALANCED WAVEFORMS

RELATED APPLICATION

The present application is a continuation of International Patent Application No. PCT/US2023/012201 filed 2 Feb. 2023, which claims priority to U.S. provisional patent application No. 63/306,162 filed 3 Feb. 2022, each of which is incorporated herein by reference in its entirety.

BACKGROUND

Field of the Invention

The present invention relates to systems and methods to generate, to deliver and to perform pulsed-field ablation with, charge-balanced waveforms.

Related Art

In the medical field, various methods and medical devices for treating a tissue based on an electrical energy and/or power are known. For example, the electrical energy/power may be used for ablating a tissue. A tissue ablation may be performed for treating and/or preventing various diseases. For example, it is known to ablate cardiac tissue for treating cardiovascular diseases (e.g., cardiac arrythmias, such as atrial fibrillation, ventricular tachycardia, etc.). The medical device in this case may, for example, be an ablation catheter. However, also other types of tissues may be treated based on an electrical energy for medical purposes with other types of medical devices.

To enable a reliable treatment, the application or source of the electrical energy/power for the tissue treatment usually needs to be controlled in a defined way to ensure a desired medical outcome for the patient. In addition to reliable treatment, minimal, or no, damage to adjacent tissue structure is also required. For example, it is known that radiofrequency ablation may produce damage to the esophagus. In some case, an atrial-esophageal fistula develops. Such condition may be life threatening.

Therefore, energy modalities that spare collateral tissues are desired. For example, a pulsed-field ablation (PFA) treatment is known to spare the esophagus, phrenic nerves, coronary structures, etc. However, if not designed optimally, PFA waveforms may cause significant skeletal muscle stimulation, which can be painful, or microbubbling, which may result in embolic events.

Hence, the currently known situation regarding generators that may be used for medical devices is not always optimal. Therefore, there is a need to find ways to improve generators for treatment of cardiac conditions by PFA.

SUMMARY

The aspects describe herein address the above need at least in part.

A first aspect relates to a generator for a substantially charge-balanced pulse for application onto at least one pair of therapeutic electrodes. The medical device may be a catheter with one or more electrodes. If the catheter carries only one electrode, a reference/return/grounding electrode could be used to close the output circuit. Alternatively, the medical device can be a hand-held surgical wand, or a surgical energy instrument. The generator may comprise a pulse-shaping output stage for coupling to the at least one pair of therapeutic electrodes. It may further comprise an internal pulse generator for applying an internal pulse to the pulse-shaping output stage. The pulse-shaping output stage may comprise a transformer and/or a capacitor system, the capacitor system comprising at least one capacitor, such that the internal pulse is transformed into a substantially charge-balanced pulse and applied to the at least one therapeutic electrode pair when coupled to said output stage.

The at least one therapeutic electrode pair may form an electrical load for the pulse-shaping output stage. The electrical load may be associated with various medical treatment modalities (e.g., a tissue treatment, e.g., a tissue ablation, a tissue stimulation, etc.) wherein the generator may be used to apply the substantially charge-balanced pulse to the treatment target. The electrical load may also be (partly) defined by a tissue and/or a path through the tissue. To illustrate an example, the least one pair of electrodes may facilitate a tissue treatment by contacting the respective tissue at a certain distance to each other. The two electrodes of a pair may thus form an electrical path through the tissue (or through the space defined by the two electrodes) wherein the electrical path may also be considered a part of the said electrical load. However, in another example, pulse-shaping output stage may apply the PFA energy to one or more single electrodes to facilitate a treatment by the medical device. Such application would be considered unipolar energy delivery, as it may involve a reference/return/grounding electrode that closes the electrical circuit. Alternatively, the PFA energy may be applied in bipolar mode to pair of electrodes located on one or more medical instruments.

A (substantially) charge-balanced output pulse may comprise that the net charge of the pulse is substantially zero. The charge-balanced pulse may for example comprise a (biphasic or multiphasic) voltage pulse having a net charge of substantially zero over a defined time window. The charge-balanced pulse may comprise a positive and a negative phase wherein the absolute value of the charge of the positive phase substantially equals the absolute value of the charge of the negative phase. The system according to this invention may also delivery pulses with multiple phases that are charge-balanced over the duration of the pulse. In another example, the charge-balanced pulse may also comprise a (biphasic or multiphasic) current pulse that has a net charge of substantially zero over the defined time window. The pulses may be high voltage pulses.

For example, a (substantially) charge-balanced pulse may comprise a (biphasic or multiphasic) voltage comprising a positive and a negative phases wherein the absolute value of the charge of the positive phases may be at least 90%, in particular at least 95%, at least 98%, at least 99% of the absolute value of the charge of the negative phases or vice versa. The charge-balanced pulse may comprise a (biphasic or multiphasic) voltage pulse having a net charge of less than ±5 µC, in particular less than ±2 µC, in particular ±1 µC over a defined time window. The defined time window may start when the positive (or negative) amplitude exceeds the measured noise level, in particular exceeds the noise level by a factor of 1.5, by a factor of 2, and may end when the negative (or positive) amplitude is below the 2 fold noise level, in particular below the 1.5 fold noise level, in particular below the noise level.

The generation of a reliable charge-balanced pulse may, for example, prevent a net charge injection into the stimulated tissue via the at least one electrode pair. Depending on the treated tissue and/or the type of treatment this may be highly beneficial. The charge balance may, for example, prevent the occurrence of electrolysis of blood, which may minimize an undesired gas generation within the organism. Generation of gas may cause microbubbling. In turn, microbubbling may lead to embolic events. For example, this may be highly beneficial when the treated tissue is within an organism such that it is surrounded by blood. The charge-balance enabled by the generator may also prevent undesired (skeletal) muscle contractions (e.g., which may be caused by direct or indirect stimulation of motor nerves). Further, the charge-balanced pulse may prevent an electrical arcing caused by ionization of the medium between electrodes of said at least one pair.

Notably, the (substantially) charge-balanced pulse may also enable a medical treatment requiring the application of a positive, as well as a negative charge. This may for example, be desired for a tissue ablation (e.g., an irreversible electroporation) the system may be configured for.

The coupling of the at least one electrode pair to the pulse-shaping output stage of the generator during an application of the charge-balanced pulse, as described herein, may be considered an active coupling of the electrode pair. For example, the medical device may comprise a plurality of electrode pairs which may be physically (e.g., mechanically) and in particular electrically connected to the pulse-shaping output stage of the generator. However, the coupling of the (substantially) charge-balanced pulse may be performed such as to selectively couple to all or only a subset of electrode pairs thereof. Such coupling may be enabled, for example, via a corresponding electrical circuit of the generator (e.g., comprising a switch) that activates all or a subset of desired electrode pairs. Such coupling that operatively couples the respective electrode pair will sometimes also be referred to as active coupling herein.

In an example, the internal pulse generator may be configured to apply an internal voltage and/or current pulse with a defined pulse duration to the pulse-shaping output stage. The internal pulse may comprise a rectangular pulse, however, also other types of internal pulses may be conceivable (e.g., a gaussian pulse, a cosine squared pulse, a Dirac pulse, a sinc pulse, etc.). The internal pulse may comprise only a positive voltage and/or only a positive current (or only a negative voltage and/or only a negative current).

The internal pulse may be applied as an input to the pulse-shaping output stage. The internal electrical pulse may then cause a (substantially) charge-balanced output pulse in the at least one coupled electrode pair. In an example, the pulse-shaping output stage of the generator may be part of a coupling circuit. Notably, the substantially charge-balanced pulse may be caused in the at least one electrode pair due to the dynamic response of the pulse-shaping output stage to the internal pulse. Notably, due to the internal pulse having a defined pulse duration the internal pulse can be considered a dynamic input to the pulse-shaping output stage. The pulse-shaping output stage may be configured to be adaptable to enable the desired dynamic response based on a given internal pulse and/or the characteristics of the electrical load that involves the at least one electrode pair. However, the characteristics of the internal pulse may also be adapted by the generator to enable the desired dynamic response of the present pulse-shaping output stage.

In an example, the pulse-shaping output stage may comprise a capacitor system with the at least one capacitor. The capacitor system may form a total capacitance of the pulse-shaping output stage. Moreover, the pulse-shaping output stage may be configured such that the total capacitance differentiates a voltage characteristic (dynamically) of the applied internal pulse. The resulting current and/or voltage characteristics in the at least one electrode pair may then result in the (substantially) charge-balanced pulse as a (dynamic) response. For example, the voltage differentiation by the total capacitance may cause an according electrical current characteristic in the at least one electrode pair. The electrical current characteristic may cause an according voltage applied to the at least one electrode pair which may correspondingly be in the form of the (substantially) charge-balanced pulse.

In an example of the generator, the at least one electrode pair may be coupled in series to the pulse-shaping output stage. For example, one electrode pair may be coupled in series with the capacitor system. The example may also comprise that one or more electrode pairs may be parallel to each other wherein said parallel circuit of electrode pairs is coupled in series to the pulse-shaping output stage. In this example, the coupling circuit may thus be considered to comprise a total capacitance in series with the total impedance of the one or more electrode pairs coupled to the capacitor system. The coupling circuit may thus form an RC-circuit. Notably, in that case, the coupling circuit may function (at least in part) as an RC differentiator circuit that transforms the internal pulse to the (substantially) charge-balanced pulse. To that regard, the voltage signal across the resistor of the RC differentiator circuit may be the voltage signal across the total impedance of the one or more electrode pairs, which forms said electrical load. Hence, the dynamic output of the RC differentiator circuit may be configured such that a (substantially) charge-balanced pulse is delivered to the one or more electrode pairs. The RC differentiator circuit may for example be constructed (or adapted) based on the characteristics of the internal pulse, the total capacitance and/or the total impedance of the one or more electrode pairs to enable the desired dynamic response.

In an example, the pulse-shaping output stage comprises the capacitor system and the generator may be configured such that at least two total capacitances of the capacitor system can be set. The total capacitance may thus be varied such that the overall electrical properties of the pulse-shaping output stage can be adapted, as well (e.g., to enable a desired dynamic response thereof). In an example, the capacitor system may comprise an electrical circuit comprising a plurality of capacitors arranged in one more circuit branches. In that case the generator and/or the capacitor system may be configured for switching one or more circuit branches on or off to set the at least two total capacitances. For example for electrical load values in the 15-25Ω range, desired capacitance values may be in the range of 0.2-0.5 μF. For loads in the 25-50Ω range, desired capacitance values may in the range of 0.1-0.2 μF. Yet for loads in the 50-150Ω range, desired capacitance values may be less than 0.1 μF. Ideally, if load values vary depending on the number of selected electrodes, the generator would adjust the capacitance value such that the equivalent time constant stays in the same range.

In another example, the generator may be configured to set at least three, preferably at least four, more preferably at least five, most preferably at least six total capacitances of the capacitor system.

In an example, the capacitor system may comprise a variable capacitor which may enable to set at least two total capacitances of the capacitor system.

In an example, the generator may be configured to set the total capacitance of the capacitor system based at least in part on an impedance of the electrical load associated with the at least one electrode pair. For example, the total capacitance may be set automatically based on the impedance of the electrical load associated with the at least one electrode pair. When one or more electrode pairs are (actively) coupled to the pulse-shaping output stage the impedance of the electrode load associated with the at least one electrode pair may comprise the total impedance of the one or more electrode pairs in the coupling circuit. The total capacitance may thus be set according to the total impedance present in the coupling circuit. For example, as outlined herein, the coupling circuit may comprise an RC circuit wherein the setting of the total capacitance enables to adjust the capacitance of the RC circuit. Also, when one electrode pair is coupled to the pulse-shaping output stage the total capacitance may only have to be set based on the impedance of the electrical load associate with the one electrode pair.

For example, the impedance of the electrical load associate with the at least one electrode pair and/or the total impedance may be measured by the generator (as described herein). The measurement may be performed based on a current and/or voltage measurement (as described herein).

In another example, the generator may be configured to receive the total impedance. The total impedance may thus be communicated to the generator such that the generator may adjust the total capacitance accordingly. For example, it may be predetermined that the active coupling of a first and second electrode pair of the medical device to the pulse-shaping output stage may result in a first total impedance wherein the active coupling of a third and fourth electrode pair may result in a second total impedance. In this example, the total impedance may, e.g., be inputted by an operator or may be received from an external device that has performed the impedance measurement.

In an example, the generator may be configured to set the total capacitance of the capacitor system based at least in part on a number of electrode pairs (actively) coupled to the pulse-shaping output stage. For example, the generator may be configured to receive the total number of electrode pairs coupled to the pulse-shaping output stage. In another example, the generator may be configured to determine the number of electrode pairs coupled to the pulse-shaping output stage. The number of electrode pairs (actively) coupled to the pulse-shaping output stage may indicate (or serve as benchmark) for the total impedance present in the coupling circuitry. Hence, the total capacitance may be set in a dependence to the total impedance present in the coupling circuit. The generator may be configured to automatically set the total capacitance of the capacitor system based on the (received or determined) number of electrode pairs. The automatic setting may be performed by an according computer program that can control the capacitor system wherein the computer program may be comprised by the generator and/or an external device. Also, the total capacitance may be manually set (e.g., by an operator) based on the number of coupled electrode pairs.

In an example, setting the total capacitance may not only be based on the number of coupled electrode pairs but also based on the medical device (or type of the medical device). The (total) impedance may not necessarily depend only on the number of coupled electrode pairs but also on the impedance of the electrical load associated with a respective electrode which may be different depending on the medical device.

In an example, the one or more electrode pairs may be parallel to each other when coupled to the pulse-shaping output stage. In this example, each impedance of an electrode pair may also be substantially the same, for example, due the design of the medical device or due to the uniformity of electrode-tissue contact. Hence, the number of electrode pairs may indicate the number of parallel branches wherein each branch comprises substantially the same impedance. A higher number of coupled electrode pairs may thus indicate a lower total impedance wherein a comparatively lower number of coupled electrode pairs may indicate a comparatively higher total impedance. Hence, the total capacitance may be accordingly adjusted. Notably, the above determination applies to both unipolar and bipolar energy applications. Unipolar energy applications require a reference/return/grounding electrode that closes the electrical circuit at the output of the generator.

For example, it may be conceivable that the total capacitance to be set by the generator is associated with a certain number of coupled electrode pairs. In that case, the generator may be configured such that when a first number of electrode pairs (of a particular medical device) is coupled to the generator, a first value of the total capacitance may be set. When a second number of electrode pairs (of the particular medical device) is coupled to the generator, a second value of the total capacitance may be set.

Notably, the electrode pairs being parallel to each other in the pulse-shaping output stage may be enabled by the generator. In an example, the generator may comprise an interface relay board for connecting the electrode pairs of the medical device to the pulse-shaping output stage. The interface relay board may comprise a (controllable, e.g., switchable) relay circuitry for coupling the electrode pairs to the pulse-shaping output stage in various ways. For example, the relay circuitry may enable to couple the electrode pairs in parallel to each other to the pulse-shaping output stage. However, in some examples, the interface relay board may also enable that the electrode pairs can be arbitrarily coupled to the pulse-shaping output stage (in series to each other, at least in part in series and at least in part in parallel, etc.). In an example of the relay board, it may comprise a first subgroup of relay channels which may be connected parallel to each other wherein each relay channel may be coupled with a first node of the pulse-shaping output stage. The relay board may comprise a second subgroup of relay channels which may be connected parallel to each other wherein each relay channel may be coupled with a second node of the pulse-shaping output stage.

In an example, the generator may be configured to set the total capacitance of the capacitor system such that a multiplication result of the total capacitance and an impedance (i.e. time constant) of the electrical load associated with the at least one electrode pair is within a predetermined range. For example, when one or more electrode pairs are coupled to the pulse-shaping output stage the impedance of the electrical load associate with the at least one electrode pair may comprise the total impedance of the one or more electrode pairs in the coupling circuit. In that case, the total capacitance and the total impedance may define an RC-circuit in the coupling circuit (as described herein). The multiplication result of the total capacitance with the total impedance may thus comprise the RC time constant $\tau$ (with $\tau = R \cdot C$, wherein R may comprise the total impedance, and C may comprise the total capacitance in that example). Hence, the generator may enable to set a desired RC time constant which may define the dynamic response of the coupling circuit. The RC time constant may be set such that a (substantially) charge-balanced pulse may be caused in the electrode pairs when the internal pulse is applied to the pulse-shaping output stage and the pulse-shaping output stage is electrically connected to the electrode pairs. This may be highly beneficial since without an according RC time constant the dynamic response may not necessarily lead to a (substantially) charge-balanced pulse. In addition, the waveform of the (substantially) charge-balanced pulse may be shaped depending on the set RC time constant. For example, it may be desirable to have a sufficient duration of the positive phase and a sufficient duration of the negative phase of the charge-balanced pulse which may be altered via the RC time constant. Furthermore, it may be desirable that both durations are substantially equal to create a (substantially) symmetric charge-balanced pulse for the medical application. Alternatively, the phase durations may be different so that to allow for the net charge to be balanced. Also, alternatively, the total capacitance value may be different for the positive and for the negative phases. This can be achieved by implementing a pulse-shaping output stage that detects the transition from positive to negative phases and drives the capacitor block to adjust its total capacitance. Accordingly, the adjustment of the RC time constant may enable to adapt the symmetry of the charge-balanced pulse since the RC time constant may function as one of the main performance parameters of the pulse-shaping output stage. Notably, some RC time constants may result in a charge-balanced pulse with two sharp positive and negative phases with a comparatively short duration, respectively, which may not always be desired depending on the medical treatment. Alternatively, one positive and one negative phase provides similar effects. Hence, the generator may be set to allow only the predetermined range of RC time constants such that extreme dynamic responses are avoided.

In another example, the generator may set the total capacitance such that a multiplication result of the total capacitance and an impedance of one electrode pair is within a predetermined range. For example, it may be necessary to adjust the RC time constant for a single electrode pair and not necessarily to the total impedance present in the coupling circuit (the whole circuit comprising the generator and all electrode pairs) to consider a desired outcome of its dynamic response. For example, this may be conceivable when the electrode pairs are coupled differently to the pulse-shaping stage than in a parallel assembly to each other. For example, unipolar vs. bipolar electrode configurations me require different time constants.

In an example, the pulse-shaping output stage may comprise the transformer such that the internal pulse is transformed into a substantially charge-balanced pulse and delivered to the at least one electrode pair when coupled to the pulse-shaping output stage. In this case the pulse-shaping output stage may comprise a part of the transformer (e.g., a coil or a winding of the transformer). This may ensure that the pulse-shaping output stage does not have a direct electrical connection (i.e. stage is not DC coupled) to the circuitry in which the high voltage internal pulse is generated. For example, a step-up transformer my be used. This may enable a galvanic isolation from the internal pulse generator. Additionally, it may boost the output voltage without placing additional voltage stress on the components of the internal pulse generator. Also in this case, the dynamic response of the coupling circuit may be adapted such that a (substantially charge-balanced pulse) is generated in the at least one electrode pair. To that regard, it may be conceivable that the inductivity of the transformer (e.g., of one of its coils) may be used in combination with the impedance of the at least one electrode pair to shape the dynamic response accordingly. For example, when using the transformer (e.g., without the capacitor system) the coupling circuit (the whole circuit comprising the generator and all electrode pairs) may comprise an RL-circuit whose dynamic response to the internal pulse can be adjusted (e.g., by adapting the inductivity L and/or the impedance R).

In an example, the pulse-shaping output stage comprises the transformer and the capacitor system, and wherein the generator is further configured such that the internal pulse is coupled from the internal pulse generator to the capacitor system via the transformer. Hence, the output of the internal pulse generator may be coupled to an input of the transformer, wherein an output of the transformer may be coupled to the capacitor system. The transformer may thus function as an intermediary element between the internal pulse generator and the capacitor system. This may enable a galvanic isolation of the capacitor system from the internal pulse generator. Moreover, a galvanic isolation from various other parts of the generator that are positioned at the input side of the transformer may also be enabled.

In an example, the transformer may be configured such that a voltage at the transformer output (which is coupled to the capacitor system) is higher than an applied voltage at the transformer input. The transformer may thus function as a step-up transformer that increases the input voltage by a predetermined amount at its output (e.g., depending on the relationship of the secondary windings to the primary windings of the transformer). The transformer may increase the input voltage by at least 10%, or 20% or by at least 30%, preferably at least 50%, more preferably at least 80%, most preferably at least 20-30%. This may be beneficial since the technical limitation of possible voltage amplitudes of the internal pulse generator may be overcome. For example, switching elements (e.g. FET transistors) of the internal pulse generator may be exposed to handling optimal current transients.

However, it may also be conceivable that the transformer may be configured such that the voltage at the transformer output (which is coupled to the capacitor system) is lower than the applied voltage at the transformer input.

In an example, the generator further comprises: means for measuring a voltage and/or a current of the at least one electrode pair when the substantially charge-balanced pulse is applied; means for determining an impedance of the at least one electrode pair based on the measurement of the voltage and/or the current. For example, the means for measuring the voltage and/or the current may be configured to measure the voltage across the at least one electrode pair (or the voltage across a plurality of parallel electrode pairs). The means for measuring may also function to measure the voltage across the total impedance of the coupling circuit (e.g., the whole circuit comprising the generator and all electrode pairs). Further, the means for measuring the voltage and/or current may be configured to measure the current within the at least one electrode (or the current supplied into a plurality of parallel electrodes). The means for measuring may also function to measure the current going through the total impedance of the coupling circuit. The voltage and/or current measurement may enable to track the applied (substantially) charge-balanced pulse, for example, during a medical treatment.

However, the voltage and/or current measurement may also be used for testing and/or calibration purposes that are not related to a medical process, as such. For example, the voltage and/or current measurement capabilities may be used for determining the impedance of the at least one electrode pair and/or the total impedance present in the coupling circuit (e.g., the whole circuit comprising the generator and all electrode pairs). Based on the determined impedance the total capacitance may be set (e.g. by the operator and/or automatically by the generator) which then may be set for the actual medical treatment. The (substantially) charge-balanced pulse used for determining the impedance may not have the same characteristics as a charge-balanced pulse that is applied during a medical treatment to avoid a medical reaction. To enable such a functionality, the electrical energy and/or power of the charge-balanced pulse applied may be set lower during an impedance measurement than during a medical treatment. For example, the amplitude of the internal pulse may be chosen lower for an impedance measurement than for a medical treatment. When the charge-balanced pulse may generally be used for an ablation treatment (e.g., an irreversible electroporation of tissue), the amplitude for the impedance measurement may be chosen such that an ablation threshold is not reached (e.g., within a margin of safety).

The means for determining the impedance may trigger the voltage and/or current measurements necessary for an impedance calculation. It may be conceivable that the impedance is determined based on a determined peak voltage, as well as the corresponding current. However, also more complex calculations may be implemented by the means for determining the impedance (e.g., calculating mean values, median values, applying a fitting algorithms, e.g. polynomial fitting algorithm, etc. of the voltage/current to determine an impedance value).

As described herein, the medical device may comprise one or more electrodes. For example, the medical device may comprise a catheter comprising the one or more electrodes. Notably, the generator may also be configured to determine the impedance (or an impedance value) of each electrode of the medical device. To enable such a functionality, one electrode of the medical device may be set as a reference electrode. For each remaining electrode the impedance is determined with respect to the reference electrode by applying a substantially charge-balanced pulse as a measurement pulse and determining the impedance as described herein. In particular, subtherapeutic charge balanced pulses may be used for determining the impedance.

In an example, the generator may not necessarily comprise the means for determining the impedance of the at least one electrode pair. It may also be conceivable that the generator may comprise only the means for measuring the voltage and/or current. For example, the means for measuring may still be triggered to perform measurements needed for determining an impedance. However, the actual calculation of the impedance may be performed by an external device that receives the impedance measurement values from the generator.

In an example, the internal pulse generator comprises a high-voltage source, wherein the generator is configured to form the internal pulse based at least in part on a high-voltage output of the high-voltage source, wherein the high-voltage source preferably can be set by the generator to provide a high-voltage amplitude of at least 1000 V, preferably at least 1500 V, more preferably at least 2000 V, most preferably at least 3000 V. The generator may thus enable to generate an internal pulse that comprises the high-voltage amplitude. The pulse-shaping output stage (or coupling circuitry) may then enable that a (substantially) charge-balanced pulse is generated having a corresponding high-voltage amplitude, as well. Notably, when the generator comprises the transformer configured as a step up transformer (as described herein) the voltage amplitude of the charge-balanced pulse may be even higher than the high-voltage amplitude provided by the high-voltage source. In an example, the high voltage amplitude provided by the generator may be in the range of 1000 V to 4000 V, 1500 V to 3500 V, 2000 V to 3000 V and/or 2500 V to 3500 V.

In an example, the internal pulse generator may comprise a high-voltage capacitor, wherein the high-voltage source is configured to charge the high-voltage capacitor. In that case, the generator may be configured to form the internal pulse based at least in part on the high-voltage amplitude of the charged high-voltage capacitor. For example, during a medical application the internal pulse generator may charge the high-voltage capacitor for a predetermined charging time such that the high-voltage capacitor may be considered to be essentially charged. One essential charge may enable to generate at least two internal pulses, preferably at least three internal pulses, more preferably at least four internal pulses, most preferably at least five internal pulses. Preferably, the capacitor system is fully charged between pulses, or, at least, between pulse trains (e.g. every heartbeat if the generator is sync-ed to the patient's cardiac cycle)

In an example, the internal pulse generator comprises a switching unit, wherein the switching unit is configured to switch the output of the high-voltage source to generate the internal pulse, wherein the switching unit preferably comprises an H-bridge circuit and/or a half H-bridge circuit. For example, the high-voltage source (and/or the high-voltage capacitor) may provide a steady output of a high-voltage amplitude. The switching unit may relay the high-voltage amplitude for a certain period of time to the pulse-shaping output stage in a first switch configuration. Subsequently, the switching unit may stop relaying the high-voltage amplitude to the pulse-shaping output stage in a second switch configuration. In an example, the second switch configuration may actively drive the input voltage at the pulse-shaping output stage to ground (e.g., to a potential of zero). Hence, an internal pulse with a defined internal pulse duration may be provided by the switching unit at the input of the pulse-shaping output stage.

The switching unit may also further comprise a power electronic circuitry or power electronic components such that the desired shape of the internal pulse may be created via the switching (e.g., a rectangular shape, a gaussian shape, a sinusoidal shape, a tooth shape, a sinc shape, etc.).

In an example, the internal pulse generator comprises a timing unit for controlling the switching unit preferably to set a timing parameter of the internal pulse and/or to set a number of internal pulses such that a train of internal pulses is applied to the pulse-shaping output stage. The timing parameter of the internal pulse may, for example, comprise a duration of the internal pulse and/or an interval between two internal pulses. The timing unit may further be configured to set a number of pulse trains wherein each train may comprise a specific number of internal pulses.

The internal pulse duration may be at least 0.5 µs, preferably at least 10 µs, more preferably at least 20 µs, most preferably at least 80 µs. Notably, the internal pulse duration set by the timing unit may be in the range of 0.5 µs to 200 µs, in the range of 1 µs to 100 µs, in the range of 1 µs to 80 µs, in the range of 1 µs to 50 µs, in the range of 1 µs to 30 µs.

The interval between two internal pulses may be at least 0.2 ms, preferably at least 0.4 ms, more preferably at least 5 ms, most preferably at least 10 ms. Notably, the interval between two internal pulses that may be set by the timing may be in the range of 0.1 ms to 20 ms, in the range of 0.2 ms to 15 ms, in the range of 0.3 ms to 12 ms, in the range of 0.4 ms to 10 ms, in the range of 0.5 ms to 10 ms.

The number of internal pulses per train may be at least 5, preferably at least 10, more preferably at least 100, e.g. at least 500. Notably, the number of internal pulses per train that may be set by the timing may be in the range of 5 to 600, in the range of 10 to 500, in the range of 20 to 500, in the range of 100 to 500, or in the range of 200 to 500.

In an example, the timing unit is configured to control the switching unit such that the internal pulse is applied based at least in part on a trigger of a medical signal. For example, the generator may be configured to receive a medical signal. The medical signal may comprise an electrocardiogram signal. In an example, the medical signal may be provided with a trigger signal which corresponds to a presence of a characteristic heart wave peak, a cardiac event and/or a cardiac cycle (e.g., an R wave peak, a QRS cycle, a P wave peak, a T wave peak, etc.). For example, the trigger signal may comprise a rectangular pulse signal wherein the rising edge of the trigger signal may correspond to a presence of the characteristic heart wave peak or cycle. For example, the internal pulse may be activated after a specific waiting time has passed after an R wave peak. The specific waiting time may be predetermined such that the internal pulses may be applied within a refractory period of the cardiac cycle.

In another example, the generator may be configured to determine the trigger in the received medical signal. Determining the trigger may be performed by the timing unit or any other suitable unit of the generator. For example, determining the trigger may comprise determining the characteristic heart wave peak, the cardiac event and/or the cardiac cycle via an according signal processing.

In an example, the generator is configured to apply a substantially charge-balanced pulse such that, if the at least one electrode pair comprises two electrodes of the medical device (e.g. in the form of a catheter system), the substantially charge-balanced pulse causes an irreversible electroporation (IRE) of a human tissue in the vicinity of (at least one of) the two electrodes. The human tissue may comprise a cardiac tissue, for example, of an atrium and/or a ventricle. However, the human tissue may also comprise a tissue of a vein and/or an artery (e.g., a pulmonary vein and/or a pulmonary artery). Notably, the generator may be adapted such that the ablation threshold for irreversible electroporation is fulfilled in the vicinity of at least one of the two electrodes. Notably, the generator may be used to drive a bipolar configuration of electrodes, as well as a unipolar configuration of electrodes of the medical device.

In an example, the generator may be configured to apply substantially charge-balanced pulses for a PFA treatment which may be based on irreversible electroporation. The generator may thus enable a controlled ablation of cardiac tissue, blood vessel tissue or any other tissue (e.g., nerve tissue, skin tissue, etc.) for a medical PFA treatment.

In an example, the generator, may comprise an interface unit for coupling to one or more external devices, such as a recording system that may for example record electrocardiographic signals obtained by the medical device. The interface unit may comprise an according output port for connecting to the one or more external devices. In an example, the interface unit may be configured to relay a signal of the at least one electrode pair to the output port (e.g. an electrocardiographic signal).

Notably, the herein described features of the generator and/or system according to other aspects of the invention may also be features and/or functionalities of the generator of the first aspect.

A second aspect relates to a catheter comprising: a connector for connecting electrode pairs of the catheter to a generator as described herein. For example, the connector may be configured such that the electrode pairs of the catheter match for a coupling with the pulse-shaping output stage. To that regard, the connector may be adapted to match with the interface relay board (as described herein), that may couple the electrode pairs to the pulse-shaping output stage of the generator in various ways.

A third aspect relates to a system comprising a generator as described herein (e.g. according to the first aspect) and a catheter as described herein (e.g. according to the second aspect).

A fourth aspect relates to a method for generating a substantially charge-balanced-pulse for application onto at least one electrode pair of a medical device, comprising: coupling the at least one electrode pair to an pulse-shaping output stage of a generator; applying a predetermined internal pulse with an internal pulse generator of the generator to generate a substantially charge-balanced pulse in the at least one electrode pair, wherein the method may be performed with a generator as described herein (e.g. according to the first aspect) and/or a system as described herein (e.g. according to the third aspect).

Notably, a further aspect relates to a computer program which may comprise instructions, that when executed by a computer, a generator of the first aspect, a catheter of the second aspect and/or a system of the third aspect, cause the computer, the generator, the catheter and/or the system to perform the method of the fourth aspect and/or a functional step associated with the method, as outlined herein. For example, the generator and/or the system may comprise means to execute the computer program instructions (e.g., a processing unit). The computer program may allow an autarkic, automated implementation of the aspects described herein. Consequently, technical intervention from medical staff may be minimized.

In an example, the computer, the generator, the catheter and/or the system may comprise one or more storage devices that may store one or more instructions that may be executed by the computer, the generator, the catheter and/or the system to perform a herein described method, functional step and/or operation of the generator, system and/or catheter.

A fifth aspect relates to a generator for a substantially charge-balanced pulse for application onto at least one electrode of a medical device, the generator comprising: means for determining an impedance of the at least one electrode by applying a substantially charge-balanced pulse. The impedance may comprise the impedance of a single electrode and/or an impedance value associated with the single electrode, for example that of the load associated with said electrode. However, the impedance may also comprise the impedance between a pair of electrodes or the total impedance of several electrode pairs. The impedance and/or the impedance value may be determined based on a current and/or voltage measurement as described herein. The aspects described above apply to both unipolar and bipolar ablation modalities.

In an example, the generator of the fifth aspect may be configured to send the determined impedance to a user interface, and/or display the determined impedance by the user interface. For example, the user interface may comprise a display (e.g., a monitor, a touchscreen, etc.) for displaying various information of the generator and/or the electrodes of the medical device.

In an example, also the generator of the fifth aspect may be configured to automatically set the total capacitance of the capacitor system comprised by the generator based at least in part on the determined impedance.

The generator according to the fifth aspect may also comprise features described herein with reference to other aspects.

In an example, a method may comprise (automatically) determining an impedance of at least one electrode and/or electrode pairs of a medical device as described herein. The method may further comprise (automatically) setting a (total) capacitance of an output capacitor system as described herein at least in part based on the determined impedance.

A sixth aspect relates to a system for coupling a substantially charge-balanced high voltage (electrical) pulse to a medical device, comprising: an output capacitor system which is configured for enabling at least two total capacitances. The system of the sixth aspect may comprise the pulse-shaping output stage as described herein. However, the system may also comprise the generator as described herein. In an example, the system of the sixth aspect may be implemented as a separate entity (e.g., as a separate board, as a separate device, etc.). In that case, the system of the sixth aspect may be for coupling to an input device wherein the input device may input the substantially charge-balanced high voltage pulse or another high voltage pulse to the system. The system may thus function as a (separate) intermediary device between, for example, the pulse generator and the medical device. Notably, the system may also transform the high voltage input pulse such that a substantially charge-balanced high voltage pulse is coupled to the medical device. As described herein, the output capacitor system of the system of sixth aspect may to that regard be coupled to an electrode pair of the medical device.

In an example, the system may be configured to set the total capacitance based at least in part on a number of electrodes of the medical device coupled to the system. The system may be configured for receiving a selection of electrodes via user interface and set the total capacitance based on the selection. The user interface may be configured to display only a selection of electrodes, in particular one or more selected sub-group(s) of all available electrodes. In another example, the system may be configured for an automatic detection of active electrodes to determine the number of coupled electrodes to the system.

In an example, the system may be configured to set the total capacitance based at least in part on a total impedance of one or more electrodes of the medical device coupled to the system. The system may be configured for receiving an impedance of the medical device and/or measure the impedance as described herein. For example, the system may comprise means for measuring the current and/or voltage of one or more electrode pairs of the medical device.

The generator according to the sixth aspect may also comprise features described herein with reference to other aspects.

A seventh aspect relates to a generator for substantially charge-balanced pulses for application onto at least one electrode of a medical device, wherein the generator is configured to apply the pulses in a manner triggered by an electro-cardiogram signal. The generator may be configured to receive the electro-cardiogram signal from an external source. The generator may thus comprise means for receiving the electro-cardiogram signal (e.g., an electronic receiving unit). The electro-cardiogram signal may comprise various signal channels which may comprise a trigger signal channel. In an example, the substantially charge-balanced pulses may be applied merely based on the trigger signal channel or the electro-cardiogram signal as such.

However, in another example the generator may be configured to receive the electro-cardiogram signal which may not necessarily comprise the trigger signal channel. Specifically, in that case the generator may comprise and/or implement an event detector that may determine cardiac events in the electro-cardiogram signal. In an example, the generator may comprise means for determining a characteristic heart wave event in the electro-cardiogram signal. In that example, the substantially charge-balanced pulses may be applied based on the detected events, e.g. as described herein. However, also a combination may be conceivable wherein the pulse application is based on the detected event by the generator and the electrocardiogram signal (e.g., the trigger signal channel).

In an example, the signal processing of the electro-cardiogram signal (and the corresponding control of the applied pulses) may be implemented by the timing unit of the generator. However, also any other computing entity of the generator may implement the signal processing of the electro-cardiogram signal (e.g., a synchronization unit, a central processing unit, a computer, a microprocessor, etc.).

In an example, the generator may comprise means for receiving a trigger instruction from a user interface, wherein the generator (or a computing entity of the generator) is configured to set a trigger signal based on the received trigger instruction and, e.g., the characteristic heart wave event (for example, the trigger signal may be set a certain amount of time after for example an R-wave peak). The pulses may then be applied by the generator according to the set trigger signal.

Notably, the generator of the seventh aspect may also comprise features or functionalities of the generator and/or system described with reference to other aspects of the invention. For example, the herein described functionalities with respect to the medical signal (in the first aspect) may be also applicable for the electro-cardiogram signal of the seventh aspect (and vice versa).

An eighth aspect relates to a generator for substantially charge-balanced high voltage pulses for application onto at least one electrode of a medical device, comprising a recording system for recording an electrical activity of the at least one electrode. The generator may further comprise an over-voltage protection element to protect the recording system from a high-voltage pulse applied to the medical device, preferably for an ablation of human tissue.

In an example, the recording of the electrical activity may be performed when no high voltage pulses are applied to the at least one electrode. The electrical activity may thus comprise the electrical activity sensed by the medical device. For example, the medical device may comprise a catheter wherein the electrodes of the catheter may also be configured for sensing, monitoring and/or mapping of electrophysiological activity (e.g., in the vicinity of the tissue contacted by the electrode). The recording system may, for example, also be used to record an electro-cardiogram signal (e.g., when the electrodes are positioned in a heart and/or in a vicinity of a heart). However, the recording system may be adapted to the voltage range and/or current range associated with sensing such that the high voltage pulse may damage the recording system. Hence, the over-voltage protection element may ensure that the recording system can reliably function over a prolonged period of time.

The over-voltage protection element may comprise one or more electrical elements to enable the protective function. For example, the over-voltage protection element may comprise switches and/or relays such that the electrode signal may be blocked during an application of pulses. The over-voltage protection element may also comprise one or more voltage suppressors (e.g., a transient voltage suppressor) to block any high-voltage signals that may be coupled to the recording system.

In another example, the recording system may be implemented by an external device which may be coupled to the generator. In that case, the generator may only comprise the over-voltage protection element such that a signal may be transmitted to the external recording device in a safe voltage range for recording purposes.

Notably, the herein described features of the generator and/or system of another aspect of the invention may also be features and/or functionalities of the generator of the eighth aspect.

It is noted that the method steps as described herein may include all aspects described herein, even if not expressly described as method steps but rather with reference to an apparatus (or device or system). Moreover, the generators (or systems or devices) as outlined herein may include means for implementing all aspects as outlined herein, even if these may rather be described in the context of method steps.

Whether described as method steps, computer program and/or means, the functions described herein may be implemented in hardware, software, firmware, and/or combinations thereof. If implemented in software/firmware, the functions may be stored on or transmitted as one or more instructions or code on a computer-readable medium. Computer-readable media include both computer storage media and communication media including any medium that facilitates transfer of a computer program from one place to another. A storage medium may be any available media that can be accessed by a general purpose or special purpose computer. By way of example, and not limitation, such computer-readable storage media can comprise RAM, ROM, EEPROM, FPGA, CD/DVD or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. The control unit as described herein may also be implemented in hardware, software, firmware, and/or combinations thereof, for example, by means of one or more general-purpose or special-purpose computers, and/or a general-purpose or special-purpose processors.

DETAILED DESCRIPTION

Subsequently, presently preferred embodiments will be outlined, primarily with reference to the above Figures. It is noted that further embodiments are certainly possible, and the below explanations are provided by way of example only, without limitation.

Figure 1:
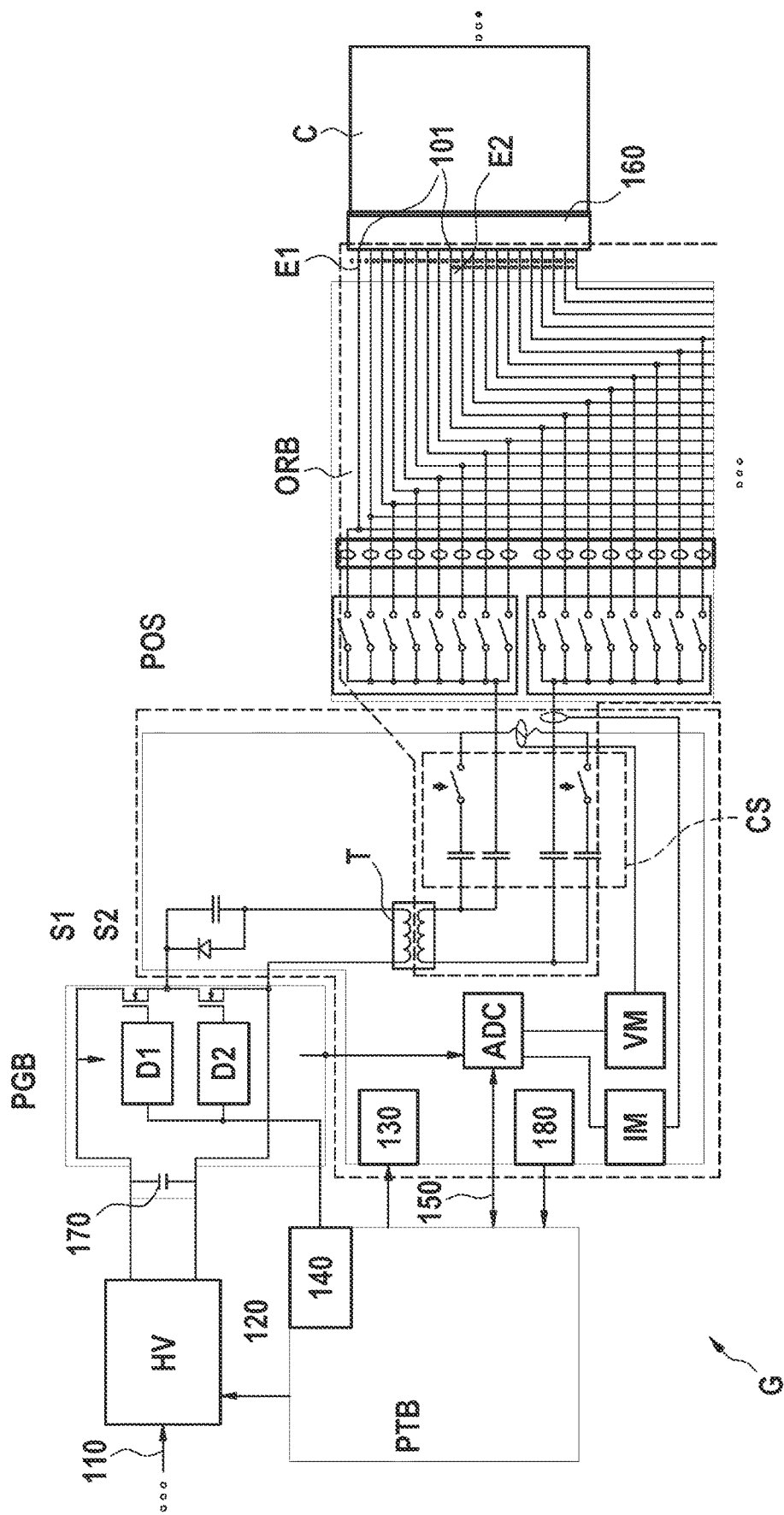
FIG. 1: Schematic representation of an exemplary embodiment of a generator according to the present invention.

FIG. 1 shows a schematic representation of an exemplary embodiment of a generator G according to the present invention. Notably, generator G of FIG. 1 may also comprise further elements not shown in FIG. 1 (but e.g. shown in FIG. 2 or 3). As outlined herein, the generator G may be used to generate substantially charge-balanced pulses for a medical device (e.g., for an ablation catheter).

The generator G may comprise a high voltage source HV. The high voltage source HV may provide a voltage of at least 1000 V. For example, the high voltage source may provide a voltage in the range of 1000 V to 4000V. In other examples, the high voltage source may also provide intermediary voltages (e.g., in the range of 100 V to 1000 V) and/or even lower voltages (e.g., in the range of 5 V to 100 V). A supply voltage may be provided via channel 110 to the high voltage source HV which may be increased by the high voltage source HV to provide the desired (high) voltage amplitude.

The generator G may comprise a pulse timing board PTB. The pulse timing board PTB may control the high voltage source HV via channel 120. For example, the pulse timing board PTB may be used to set the voltage amplitude of the high voltage source HV. The pulse timing board PTB may also be used to set the current provided by the high voltage source HV.

The generator may comprise a pulse generation board PGB which may be coupled to the high voltage source HV. The pulse generation board PGB may comprise a high voltage capacitor 170. During operation the high voltage source may charge the high voltage capacitor 170. The high voltage capacitor 170 may thus be used as the energy and/or power source for generating the internal pulse, as described herein.

The pulse generation board PGB may comprise a switching unit. In the example of FIG. 1 the switching unit may comprise a half H-bridge circuit. The half H-bridge circuit of FIG. 1 comprises a first switch S1 and a second switch S2. The switches S1, S2 may be switched via the drivers D1 and D2, respectively. However, also another switching circuit may be used in the generator G (e.g., a H-bridge circuit, or another suitable switching configuration). The drivers D1, D2 of FIG. 1 may be controlled by the pulse timing board PTB via its driver control unit 140 which may be connected to the drivers D1, D2. The switching may enable to generate a reliable internal pulse that may be coupled as an input to the pulse-shaping output stage POS of the generator.

The pulse-shaping output stage (POS) may comprise a transformer T (as described herein) at its input. The transformer T may function as a step-up transformer such that the voltage at the input of the transformer T is increased at the output at the transformer by a defined ratio. Further, the pulse-shaping output stage POS may comprise a capacitor system CS (as described herein). The output of the transformer T may be coupled to the capacitor system CS. The capacitor system CS may comprise various branches with one or more capacitances. The capacitance of a branch may be activated by a switch, as exemplarily indicated in FIG. 1. The switches may be controlled via the capacitor switching unit 130, which may be controlled by the pulse timing board PTB. The generator G may be configured to set at least two total capacitances for the capacitor system CS, as described herein. Notably, the generator may be configured to set a wider plurality of capacitances (e.g., at least three, at least 5, at least 10, at least 50 total capacitances) depending on the chosen circuit of the capacitor system CS. The transformer T and the capacitor system CS may function as the pulse-shaping output stage, as described herein.

The output of the pulse-shaping output stage POS may be coupled to an output relay board ORB of the generator G. The output relay board ORB may couple the output of the pulse-shaping output stage POS in a controlled manner to at least one electrode pair 101 of the medical device C. The medical device C may comprise one or more electrodes (e.g., two electrodes), as outlined herein. The electrode pair may thus be considered a load that can be driven by the generator. In the example, of FIG. 1 each electrode of the medical device C may be individually coupled to the output relay board ORB. As can be seen in FIG. 1, the output relay board ORB is adapted for coupling the paths of sixteen electrodes to the generator, wherein four electrodes are coupled to a different part of the generator (for recording purposes, as described herein). The exemplary electrode pair 101 may comprise the connection of the path of a first electrode E1 (the first of the odd numbered electrodes) with the path of the first of the even numbered electrodes E2. A defined voltage and/or current may thus be applied between the first electrode E1 and the second electrode E2 as the two terminals may be controlled via the generator. Notably, the two terminals are relayed into the pulse-shaping output stage POS such that they may form at least a resistive part of the pulse-shaping output stage.

The output relay board ORB may comprise one or more relay switches to actively couple one or more desired electrode pairs to the pulse-shaping output stage POS. The output relay board ORB may comprise a first relay switch group that may be coupled to a first number of electrodes of the medical device C (e.g., 8 electrodes as indicated in FIG. 1). The first relay switch group may connect the first number of electrodes to a first node of the pulse-shaping output stage depending on the switch configuration. The output relay board ORB may also comprise a second relay switch group that may be coupled to a second number of electrodes of the medical device C (wherein the second number may equal the first number, e.g., 8 electrodes as indicated in FIG. 1). The second relay switch group may connect the second number of electrodes to a second node of the pulse-shaping output stage depending on the switch configuration. Hence, a defined voltage and/or current may be applied between the electrodes associated with the first relay switch group and the electrodes associated with the second relay switch group. Moreover, a substantially charge-balanced pulse may be applied across the electrodes coupled to different relay switch groups.

By coupling the electrode pairs to the pulse-shaping output stage a coupling circuit may be formed, as described herein. The coupled electrode pairs may then function (in total) as a resistive part of the coupling circuit. The coupling circuit may thus also be understood as an RC-circuit, as described herein. The total impedance of the coupled electrode pair may thus be considered as the resistivity R of the RC-circuit. As indicated in FIG. 1 the output relay board may couple various electrode pairs parallel to each other to the pulse-shaping output stage (via the relay switch circuitry). It can also be seen in FIG. 1 that the parallel arrangement of the electrode pairs may be coupled in series to the capacitance of the capacitor system CS. The total impedance of the coupling circuit may thus be defined by a parallel circuit of the electrode pairs. Notably, the capacitor system CS may comprise two capacitor sub systems (as indicated in FIG. 1). The electrode pairs may, for example, be coupled in series between the first capacitor sub system and the second capacitor sub system.

The output relay board ORB may further comprise an interface unit 160 which may facilitate the mechanical and/or communicative coupling of the output relay board ORB to the connector of the medical device C.

Subsequently, the generation of the substantially charge-balanced pulse is discussed. To generate an internal pulse as an input to the pulse-shaping output stage POS the voltage of the high voltage source needs to be applied for a specific time duration. This may be achieved in a controlled way by the switching of the switches S1, S2.

For example, when switch S1 is closed (and switch S2 is open) the high voltage provided by the high voltage capacitor 170 may be coupled to the input of pulse outcoupling board POB of the generator G. For example, the high voltage may then be applied at the transformer T. When switch S1 is open and switch S2 is closed, the voltage at the input of the pulse-shaping output stage POS (e.g., at the input of the transformer T) is actively set to ground. Hence, a defined pulse duration of the internal pulse may be achieved.

As described herein, by coupling the one or more electrode pairs to the pulse-shaping output stage a coupling circuit (e.g., an RC-circuit) is formed. The dynamic response of the coupling circuit to the internal pulse may cause a substantially charge-balanced pulse to be applied in the coupled one or more electrode pairs. Thereby, a substantially charge-balanced pulse is applied via the electrodes, as well. Hence, the coupled medical device C may be used to apply charge-balanced pulses with a high voltage (e.g., onto a tissue for an ablation procedure).

The generator G may further comprise means for measuring the voltage and/or current, e.g., to determine the impedance of the coupled electrode pairs. For example, the pulse-shaping output stage POS may comprise a voltage measurement unit VM. The voltage measurement unit VM may pick up the voltage across the coupled electrode pairs. For example, the voltage may be measured across the parallel circuit of the electrode pair caused by the output relay board ORB (as indicated in FIG. 1). For example, the measured voltage may be associated with the voltage applied across the (total) impedance R of the RC-circuit formed by the coupling circuit.

The pulse-shaping output stage POS may also comprise a current measurement unit IM. The current measurement unit IM may pick up or measure the current in series to the coupled electrodes (e.g., in series to the parallel circuit of the electrode pairs). For example, the measured current may be associated with the current flowing through the RC-circuit (e.g., the current going through the (total) resistivity R).

For enabling an impedance measurement, instead of the described high voltage pulses, e.g. an internal pulse with an intermediary voltage range or a lower voltage range (as described herein) may be applied. This may ensure that the actual high voltage application (which may have a permanent medical effect) is not performed during an impedance measurement. However, during an impedance measurement also a substantially charge-balanced pulse may be triggered in the one or more electrode pairs.

The voltage and/or current measurement data (e.g., of an impedance measurement) may be converted to digital data for an analysis thereof via the analog-to-digital converter ADC of the pulse-shaping output stage POS. Notably, the ADC may also be used to convert analog data of a high voltage sense HV sense of the pulse generation board PG to digital values for further analysis. The measurement results of the voltage measurement unit VM and the current measurement unit IM may be further processed by the generator G. The pulse-shaping output stage POS may also comprise an open circuit shut unit 180. The open circuit shut unit 180 may determine whether an open circuit is present in the coupling circuit (e.g., this may be the case if no electrode pair is actively coupled to the pulse-shaping output stage POS). The presence of an open circuit may be communicated to the pulse timing board PTB which may be configured to not apply an internal pulse if an open circuit is present.

The current and/or voltage measurement results may be used to determine the total impedance of the coupled electrode pairs. To that regard, the voltage drop across all actively coupled electrode pairs may be measured. Furthermore, the current going through the total impedance may be measured by the current measurement unit. Hence, the measurement information may enable to determine an according total impedance. The calculation of the impedance may be performed by the pulse-shaping output stage POS, by the pulse timing board PTB and/or any other suitable processing entity of the generator G (e.g., a processing unit).

For measuring an impedance value of an electrode one electrode may be set as a reference electrode. For example, the second electrode E2 (coupled to the second relay switch group) may function as a reference electrode. Subsequently, each electrode of the first relay switch group may be (separately) activated for a corresponding voltage and current measurement via an applied measurement pulse. For example, a first circuit may be formed between the first and second electrode for an impedance measurement of the first electrode, a second circuit may be formed between the third and fourth electrode for an impedance measurement of the third electrode, and so forth.

The generator G may then analyze the measurement values received from the measurement units VM and IM. Based on the peak voltage and the measured peak current value the impedance value may be determined for each electrode separately. Also, a mean value may be determined for each electrode if the peak current is determined from more than one voltage pulse for each electrode.

The same mechanism may be applied to measure the impedance for the electrodes that are connected to the second relay switch group wherein the reference electrode may be an electrode connected to the first relay switch group, and/or electrode pairs e.g. from the first and second relay switch groups.

Notably, the output relay board ORB may comprise various other switching capabilities. The impedance measurement for the electrodes may also, for example, be performed for a single reference electrode, and separate impedance measurements may be performed for the remaining electrodes.

The information about the impedance of the actively coupled electrode pairs may be used to adjust the total capacitance of the capacitor system CS. For example, a desired RC time constant may be set for the RC-circuit that falls within a desired range. Adapting the time constant may ensure a sufficient control of the evoked charge-balanced pulse (e.g., a desired dynamic response, a desired symmetry of the charge-balanced pulse). As stated, the impedance measurement may be used to determine the total impedance for the actively coupled electrode pairs that may be coupled during a medical treatment. The RC time constant T may be defined as $\tau = R \cdot C$ (wherein R may comprise the total impedance, and C may comprise the total capacitance of the coupling circuit). Accordingly, with a desired RC time constant $\tau_S$ the (ideal) total capacitance $C_S$ to be set may be defined as $C_S = \tau_S/R$. As it may not always be necessary to have a specific RC time constant value, the total capacitance may be chosen such that the RC time constant falls within a predetermined range. For example, the RC time constant may be chosen to fall in the range of $0.5 \cdot 10^{-6}$ s to $30 \cdot 10^{-6}$ s. Notably, the RC time constant may also be chosen to be in the range of $3 \cdot 10^{-6}$ s to $8 \cdot 10^{-6}$ s.

The generator G may be configured to automatically set the capacitance of the capacitor system based on the determined total impedance such that the RC time constant may fall within the predetermined range. Alternatively, the generator G may be configured to set a capacitance based on a value of the determined total impedance. For example, if the total impedance may fall in a first range (e.g., between 15 Ohm and 25 Ohm), the generator may set a first total capacitance (e.g., between 0.2 µF and 0.5 µF). If the total impedance may fall in a second range (e.g., between 25 Ohm and 50 Ohm), the generator may set a second total capacitance (e.g., between 0.1 µF and 0.3 µF). If the total impedance may fall in a third range (e.g., between 50 Ohm and 200 Ohm), the generator may set a third total capacitance (e.g., between 0.01 µF and 0.15 µF).

The set total capacitance may then be the total capacitance used in the pulse-shaping output stage when a medical treatment is performed via the electrodes of the medical device C (e.g., an ablation procedure).

Figure 2:
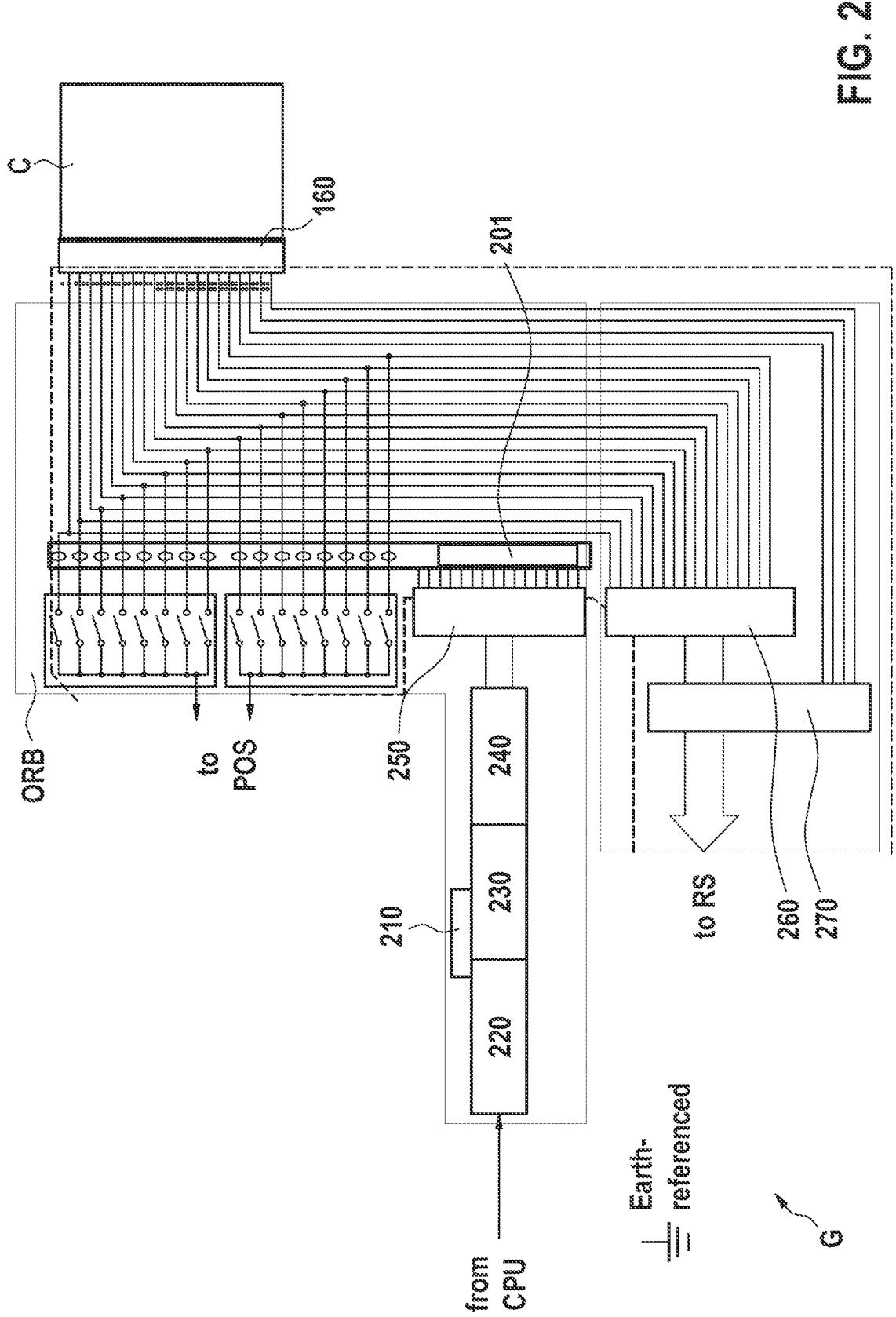
FIG. 2: Schematic representation of an output relay board of the exemplary embodiment of the generator.

FIG. 2 shows a schematic representation of an output relay board ORB of the exemplary embodiment of the generator. FIG. 2 shows the output relay board ORB of FIG. 1 to a fuller extent. The output relay board ORB may comprise a current sensor unit 201. The current sensor unit 201 may comprise one or more current sensors for sensing the current of an electrode. The output relay board ORB may also comprise a channel current measurement unit 240. The channel measurement unit 240 may be communicatively connected to the current sensor unit 201 (e.g., to receive the sensed current of the electrode pairs). The channel current measurement unit 240 may be configured to determine (or measure) the current for each coupled electrode pair based on the sensed current by the current sensor unit 201. The channel current measurement unit 240 may be coupled to a peak detection unit 250. The peak detection unit 250 may be communicatively connected to the current sensor unit 201 (e.g., to receive the sensed current of the electrode pairs). The peak detection unit 250 may be used for determining current peaks (and/or voltage peaks) in the electrode pairs based on the sensed current by the current sensor unit 201. The peak detection unit 250 may be communicatively coupled to the channel current measurement unit 240. For example, the current sensor unit 201, the channel current measurement unit 240 and the peak detection unit 250 may be used to determine the peak current when determining the impedance of an electrode, as described herein.

The output relay board ORB may further comprise an FPGA unit 220. The output relay board ORB may also comprise an ADC unit 230 which may comprise one or more ADCs. The ADC unit 230 may be used to convert the analog signal of the channel current measurement unit 240 to a digital signal for a processing thereof. The FPGA unit 220 and the ADC unit 230 may also be part of a switch relay control unit 210. The switch relay control unit 210 may be configured to control the relays and their configuration within the output relay board ORB (e.g., for closing and/or opening relay switches). For example, the switch relay control unit 210 may control the coupling of the electrode pairs to the pulse-shaping output stage POS. For example, the switch relay control unit 210 may control the relays of the first and second relay switch group.

Figure 3:
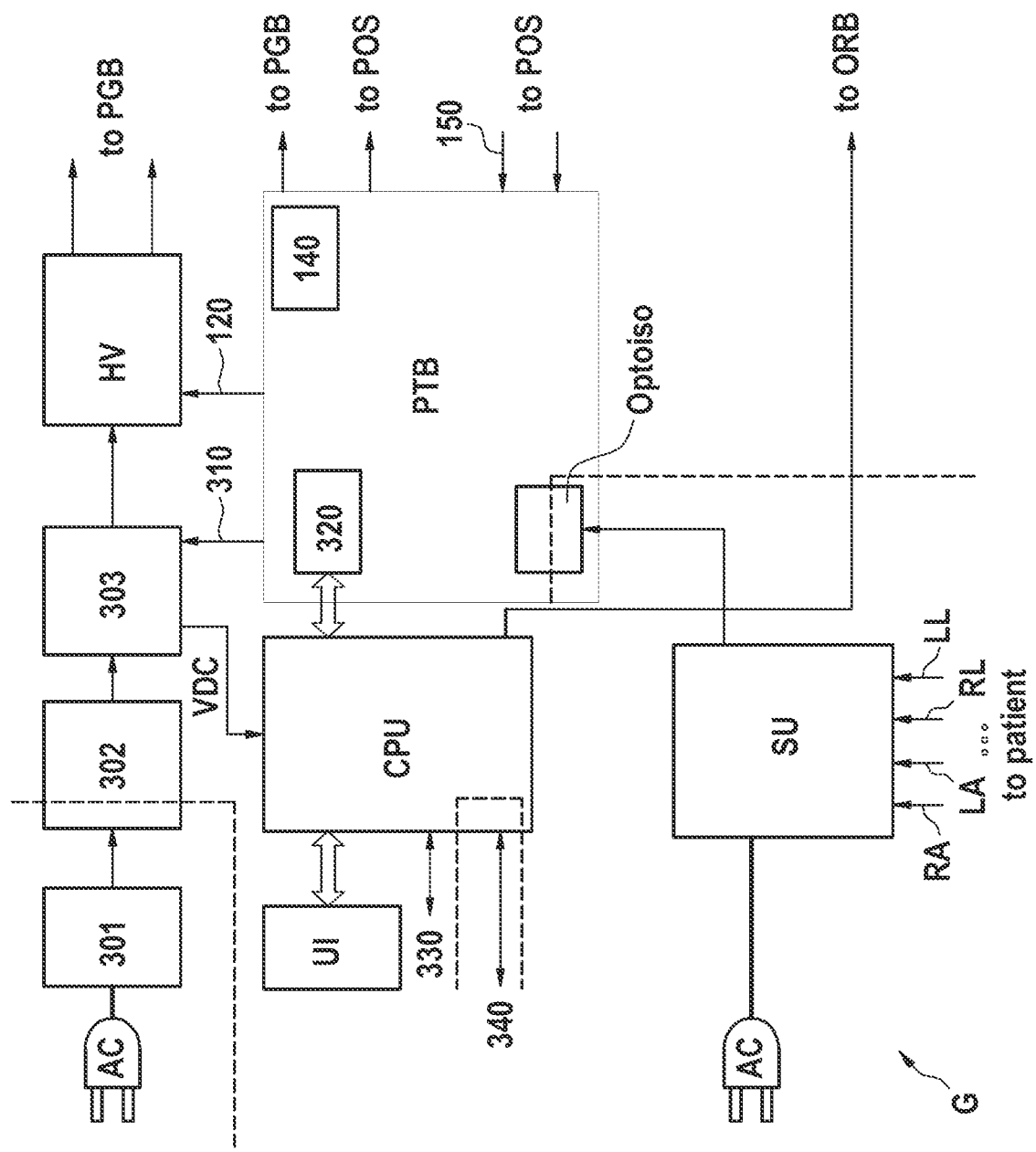
FIG. 3: Schematic representation of various components of the exemplary embodiment of the generator.

The output relay board ORB may be controlled by one or more central processing units CPU of the generator G. The one or more central processing units CPU may control the components of the output relay board ORB (e.g., of the switch relay control unit 210). An exemplary central processing unit CPU is shown in FIG. 3.

Coming back to FIG. 2, the output relay board ORB may further comprise a connection to a recording system RS. The output relay board ORB may comprise paths that connect the electrodes (or the electrode channels) of the medical device C to the recording system RS. Hence, the signal of the electrodes may be transmitted to the recording system RS. In another example, the generator G may comprise the recording system RS.

As can be seen in FIG. 2, the output relay board ORB may comprise a first over-voltage protection element 260. The first over-voltage protection element 260 may be for coupling to the electrodes of the medical device C that may perform a high voltage application (e.g., a tissue ablation). The first over-voltage protection element 260 may comprise relay switches that may close or open the path from the signal of the electrodes to the recording system RS. An open relay may not allow any signal to be transmitted from the electrodes (e.g., ablation electrodes) to the recording system RS. Hence, a signal with a high voltage may not be transmitted to the recording system if the relay switches are open during a high-voltage application.

The output relay board ORB may also comprise a second over-voltage protection element 270. The second over-voltage protection element 270 may be also coupled to the first over-voltage protection element 260 to enable additional support for its protective functionality. Notably, the second over-voltage protection element 270 may be directly for coupling to sensing electrodes of the medical device C, as indicated by FIG. 2. The second over-voltage protection element 270 may comprise a transient voltage suppressor.

FIG. 3 shows a schematic representation of various components of the exemplary embodiment of the generator. Notably, the components may be components of the same exemplary generator shown partly in FIG. 1 and FIG. 2. For example, in FIG. 3 the pulse timing board PTB, as well as the high-voltage source HV of FIG. 1 are shown, as well. Notably, the connection to the pulse generation board PGB, the connection to the pulse-shaping output stage POS, the connection to the output relay board ORB of the generator G are shown in FIG. 3.

For generating the voltage for the pulse, the generator G may comprise various stages prior to the high-voltage source HV. For example, the generator G may comprise a power entry module 301 that may be for coupling to an alternating current AC-supply. The power entry module 301 may be coupled to a DC power supply 302. The DC power supply 302 may adapt the alternating current AC supply such that a DC voltage may be provided. For example, the DC power supply 302 may provide a DC voltage of 48 V. The DC power supply 302 may be coupled to a DC-DC converter 303. The DC-DC converter 303 may further increase the DC voltage provided by the DC power supply 302. For example, the DC-DC converter 303 may provide a voltage of 400 V. However, also other voltage may be conceivable (e.g., in the range of 100 V to 800V). The DC-DC converter 303 may be controlled by the pulse timing board PTB (e.g., to set the output voltage of the DC-DC converter 303). The DC-voltage at the output of the DC-DC converter 303 may be provided at the input of the high voltage source HV. The high-voltage source HV may use the provided input voltage to create a high voltage at its output. The output of the high-voltage source may then be coupled to the pulse generation board PGB, as described herein.

The generator G may comprise a central processing unit CPU. The central processing unit may be provided with voltage from the DC-DC converter 303. However, the voltage provided for the central processing unit CPU may be different than the voltage at the output of the DC-DC converter 303. For example, the central processing unit CPU may be provided with 24 V (or 12 V) by the DC-DC converter 303.

The central processing unit CPU may be communicatively connected to various components of the generator G and/or external components. For example, the central processing unit CPU may be communicatively coupled to the pulse timing board PTB and/or to the output relay board OTB. Moreover, the central processing unit CPU may be communicatively coupled to the pulse generation board PGB and to the pulse-shaping output stage POS via the pulse timing board PTB. Hence, the central processing unit CPU may receive various information from components of the generator G and/or may send various instructions to components of the generator G. For example, the central processing unit CPU may receive the current and/or voltage values of an impedance measurement and perform the necessary calculations to determine an according impedance (as described herein).

The central processing unit CPU may be coupled to a user interface UI. The central processing unit CPU may thus receive information from the user interface UI and/or communicate information to the user interface UI for a display thereon. For example, the central processing unit may receive a selection of electrodes of the medical device (which for example, may be inputted by a medical staff) from the user interface UI. The central processing unit CPU may then, for example, communicate instructions to activate the components of the generator G such that the according electrodes are actively coupled (e.g., via the output relay board). The central processing unit CPU may also communicate the results of the impedance measurement (e.g., the total impedance and/or the impedance of the electrodes, as described herein) to the user interface UI. The central processing unit may also perform the necessary calculations to determine what total capacitance should be set in the capacitor system CS by the pulse-shaping output stage. For example, based on determined total impedance the central processing unit CPU may calculate the appropriate total capacitance (or alternatively simply based on the number of actively coupled electrodes). Subsequently, an according control signal may be sent to the pulse-shaping output stage POS to set the appropriate total capacitance. For example, the RC times constants (or the sufficient range of the RC time constants) may also be input via the user interface to the central processing unit. This information may then be used by the central processing unit CPU to enable a setting of the total capacitance with respect to the total impedance and a suitable RC time constant. Additionally or alternatively, these may be stored during manufacture. The user interface may also be used to display the set total capacitance by the generator. Notably, various other technical and/or medical information may be communicated to the user interface for a display thereon.

In an example, the central processing unit CPU may receive a trigger instruction from the user interface UI. For example, the generator G may be for coupling to a synchronization unit SU. The synchronization unit SU may also be comprised by the generator G. The synchronization unit SU may receive an electrocardiogram signal from a patient, preferably, from a patient who receives the medical treatment performed via the medical device C that the generator G supplies the charged balanced pulses to. The synchronization unit SU may receive electrical activities from various electrocardiogram electrode leads, for example from electrodes positioned at the right arm RA, the left arm LA, the right leg RL, the left leg LL. The synchronization unit SU may determine characteristic cardiac events (e.g., an R wave peak, a QRS cycle, etc.). The synchronization unit SU may also provide a trigger signal with the electrocardiogram signal. For example, for an R-wave peak a rising flank may be provided in the trigger signal. The trigger instruction that may be input to the user interface UI may comprise a trigger time interval. After the occurrence of a specific cardiac event the trigger time interval may be the time span after which the internal pulse (or the train of internal pulses) should be generated. This may ensure that the application of the substantially charge-balanced pulses via the electrodes of the medical device C is synchronized to a cardiac event. For example, the time interval may be chosen such that the substantially charge-balanced pulses are applied in a refractory period of the cardiac cycle (and in one or more periods in between two refractory periods, capacitor 170 may be recharged, for example). It may also be conceivable, that the characteristic cardiac event serving as the trigger may be input to the user interface UI or displayed by it. The synchronization unit SU may be directly coupled to the pulse timing board PTB. The electrocardiogram signal and/or its trigger signal may thus be directly communicated to the processing entity that controls the timing of the pulse. The trigger time interval (and/or the according characteristic event) may be stored in the pulse timing board PTB, wherein the trigger time interval was communicated thereto by the central processing unit. Notably, FIG. 3 also indicates the optical isolation of the pulse timing board PTB with respect to the input of the synchronization unit.

In an example, the central processing unit CPU may be configured to determine the characteristic cardiac event within the electrocardiogram signal and may create the trigger signal itself. In that case, the synchronization unit SU may be directly communicatively connected to the central processing unit CPU.

The central processing unit CPU may also comprise various connective capabilities. For example, the central processing unit CPU may comprise a USB connection 330. The central processing unit CPU may also comprise an iso ethernet connection 340.

Figure 4A:
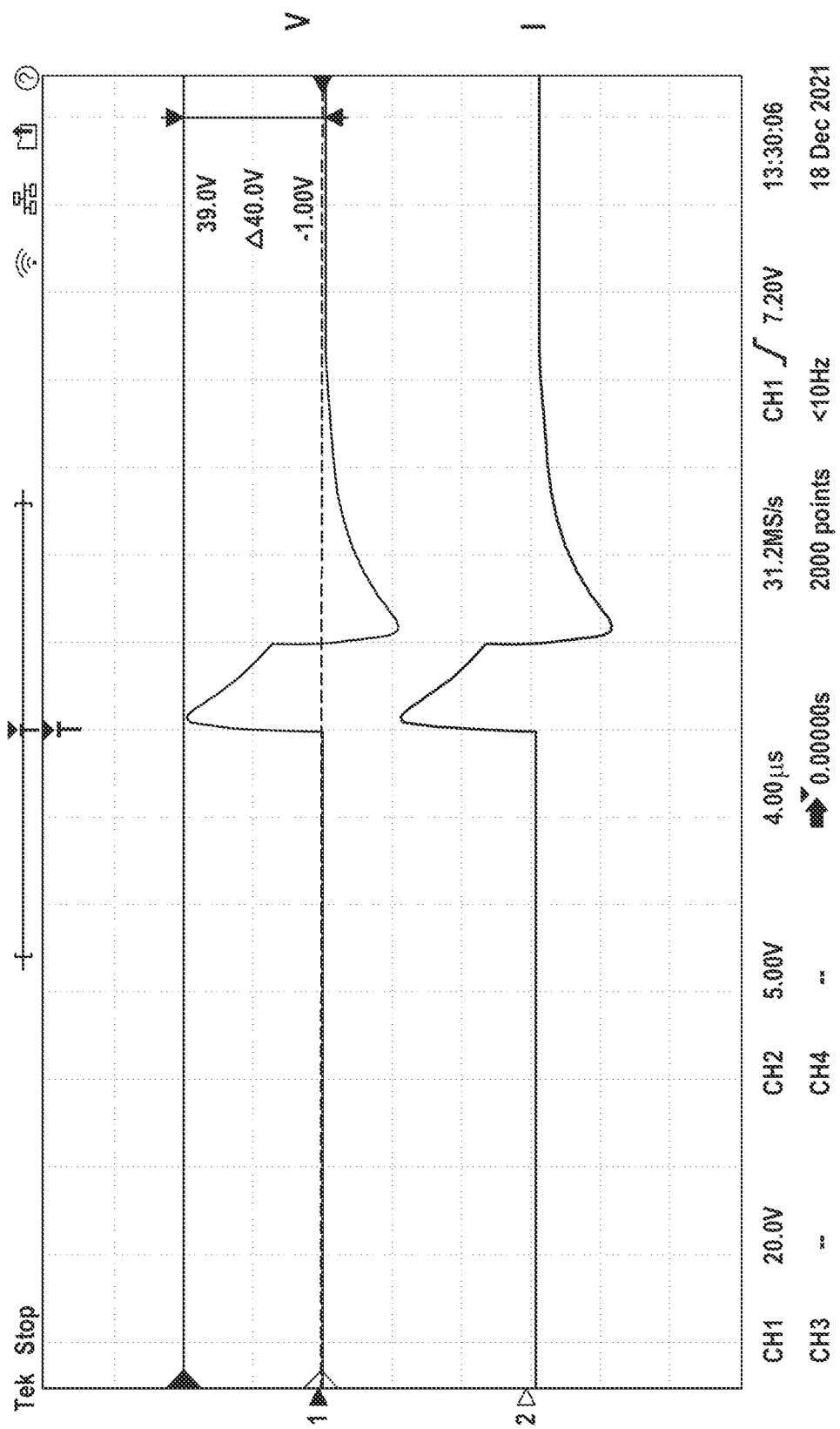
FIG. 4a/b: Representation of a first example of a charge-balanced voltage and current pulse implemented by a generator according to the invention.
Figure 4B:
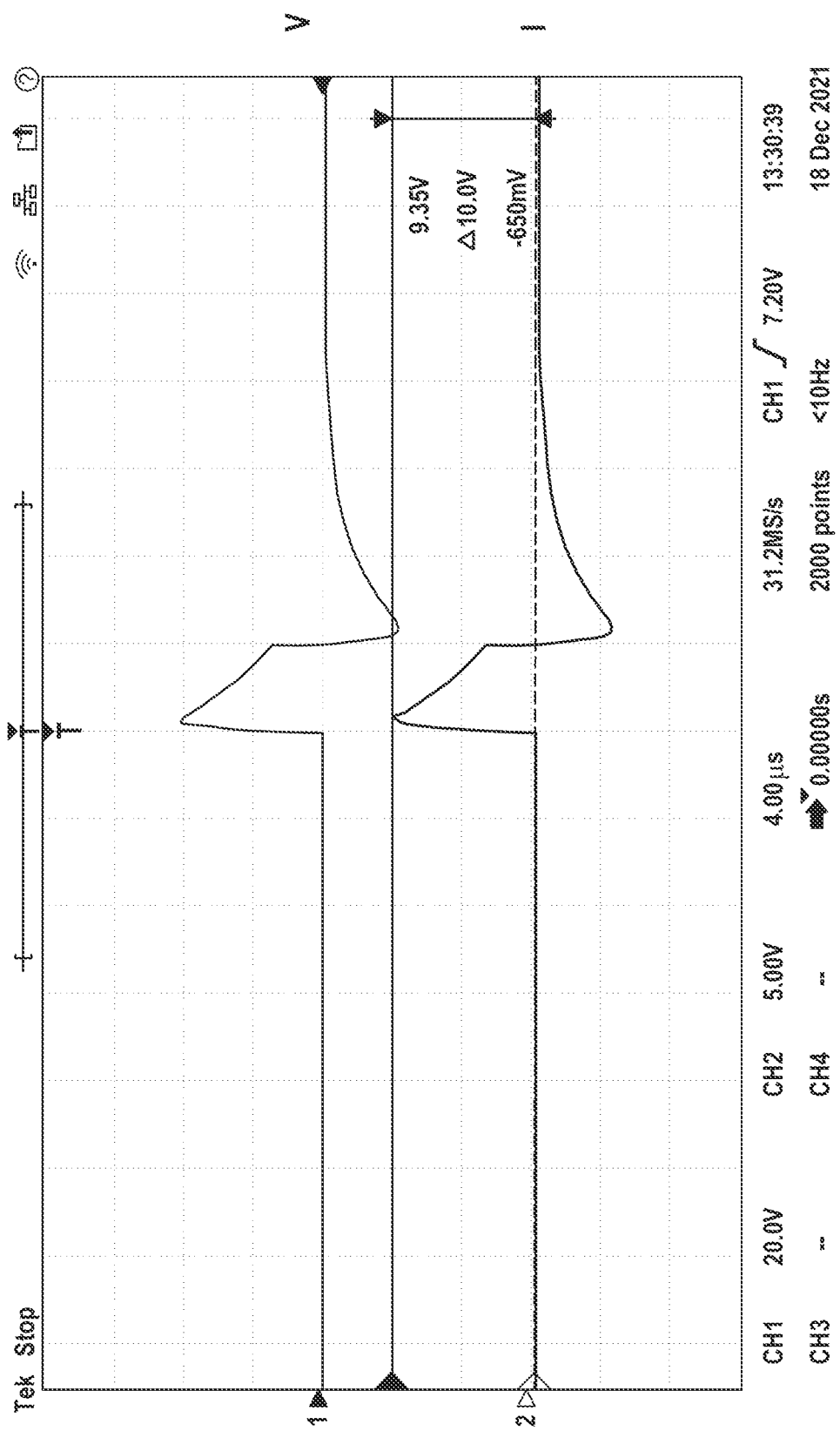

FIG. 4*a/b* shows a representation of a first example of a charge-balanced voltage and current pulse applied by electrodes of the medical device C wherein the pulse is provided to the electrodes by a generator G according to the invention. Channel 1 depicts the pulse voltage V which is scaled down by a factor of 100 (e.g., 40 V on channel 1 represent 4000 V of pulse voltage). Channel 2 depicts the resulting current I displayed as a voltage which is scaled down by a factor of 10 (e.g., 10 V on channel 2 represent 100 A of pulse current). In FIG. 4*a/b* four electrode pairs were actively coupled to the generator. The total impedance in the coupling circuit was determined as 40 Ohm. The total capacitance was set to 0.13 µF. It can be seen that a biphasic pulse was generated, with a positive and a negative section. Regarding the voltage characteristics, the amplitude of the voltage pulse in this example may peak at about +4000 V and at about −2000V. Regarding the current characteristics, the amplitude of the current pulse in this example may peak at about +100 A and at about −60 A. The exemplary pulse shown on the oscilloscope display may be used as a suitable PFA waveform for a tissue ablation. Due to the circuitry in the generator G a substantially charge-balanced pulse as a PFA waveform can be reliably ensured.

Figure 5A:
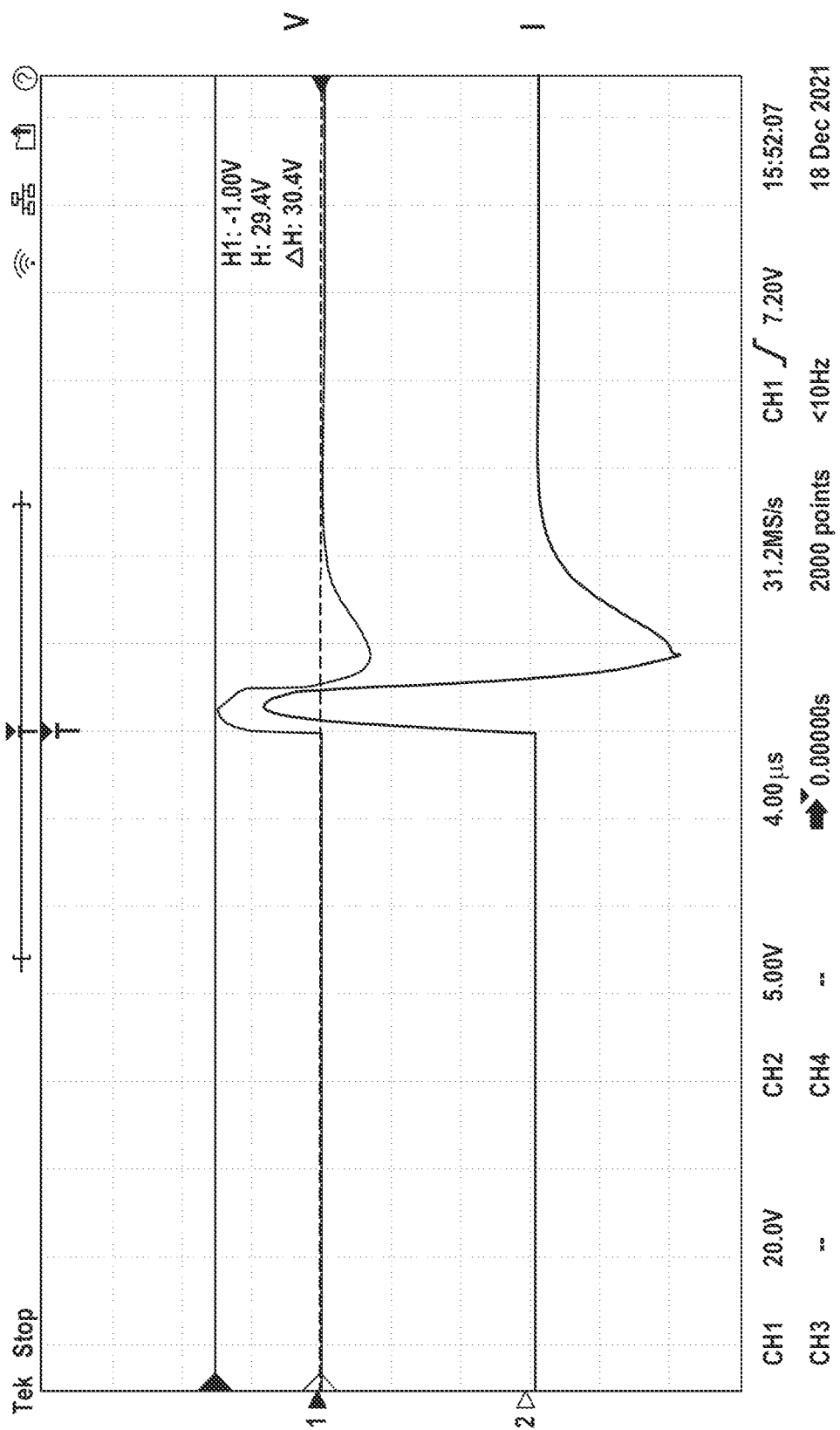
FIG. 5a/b: Representation of a second example of a charge-balanced voltage and current pulse implemented by a generator according to the invention.
Figure 5B:
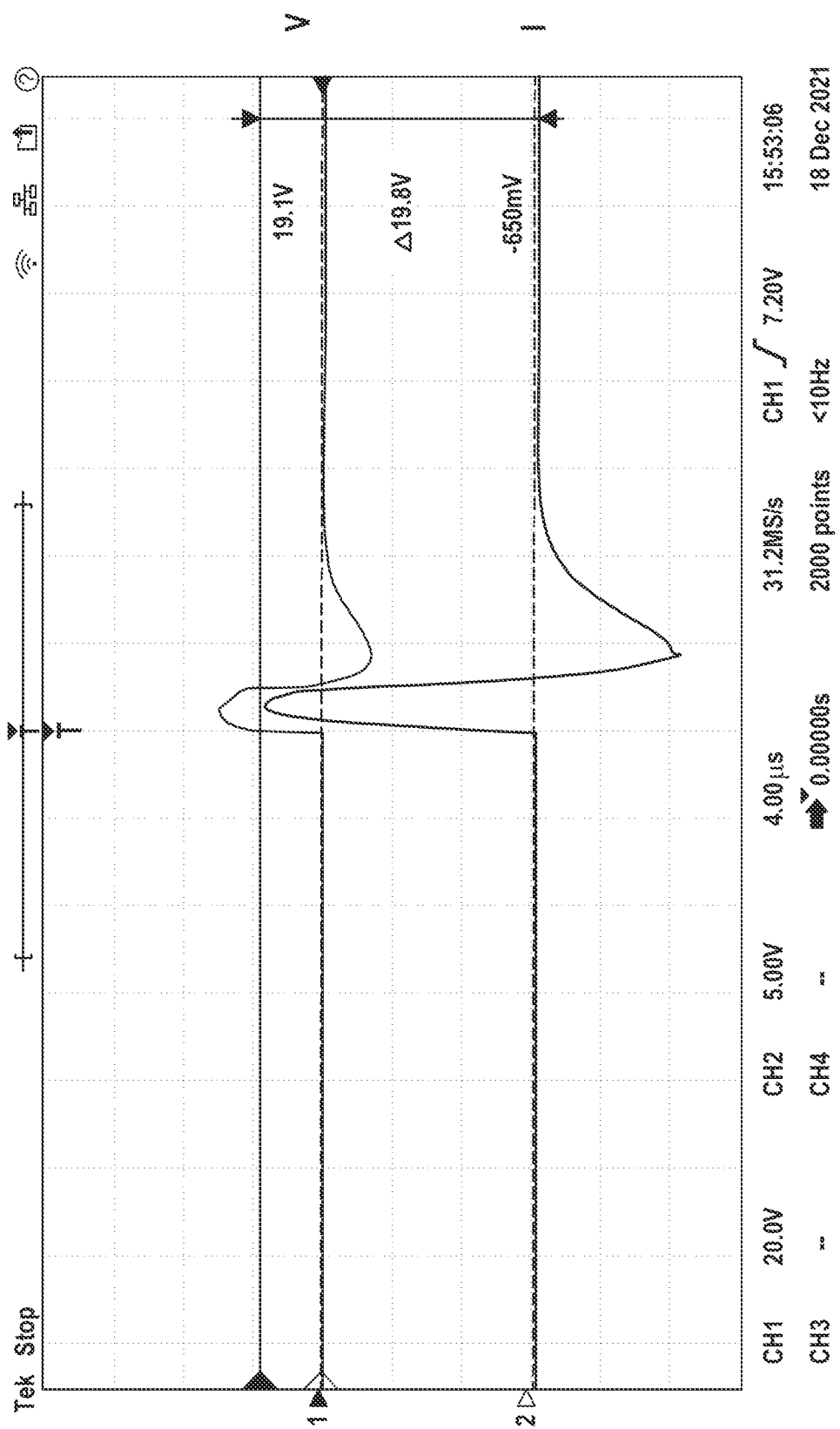

FIG. 5*a/b* shows a representation of a second example of a charge-balanced voltage and current pulse implemented by a generator according to the invention. The channel scaling corresponds to the channel scaling of FIGS. 4*a/b*. In FIG. 5*a/b* eight electrode pairs were actively coupled to the generator. In this example, the total impedance was determined as 15 Ohm. The total capacitance was set to 0.34 µF. Regarding the voltage characteristics, the amplitude of the voltage pulse in this example may peak at about +2940 V and at about −1200V. Regarding the current characteristics, the amplitude of the current pulse in this example may peak at about +198 A and at about −100 A. The exemplary pulse shown on the oscilloscope display may also be used as a suitable PFA waveform for a tissue ablation.

Figure 6A:
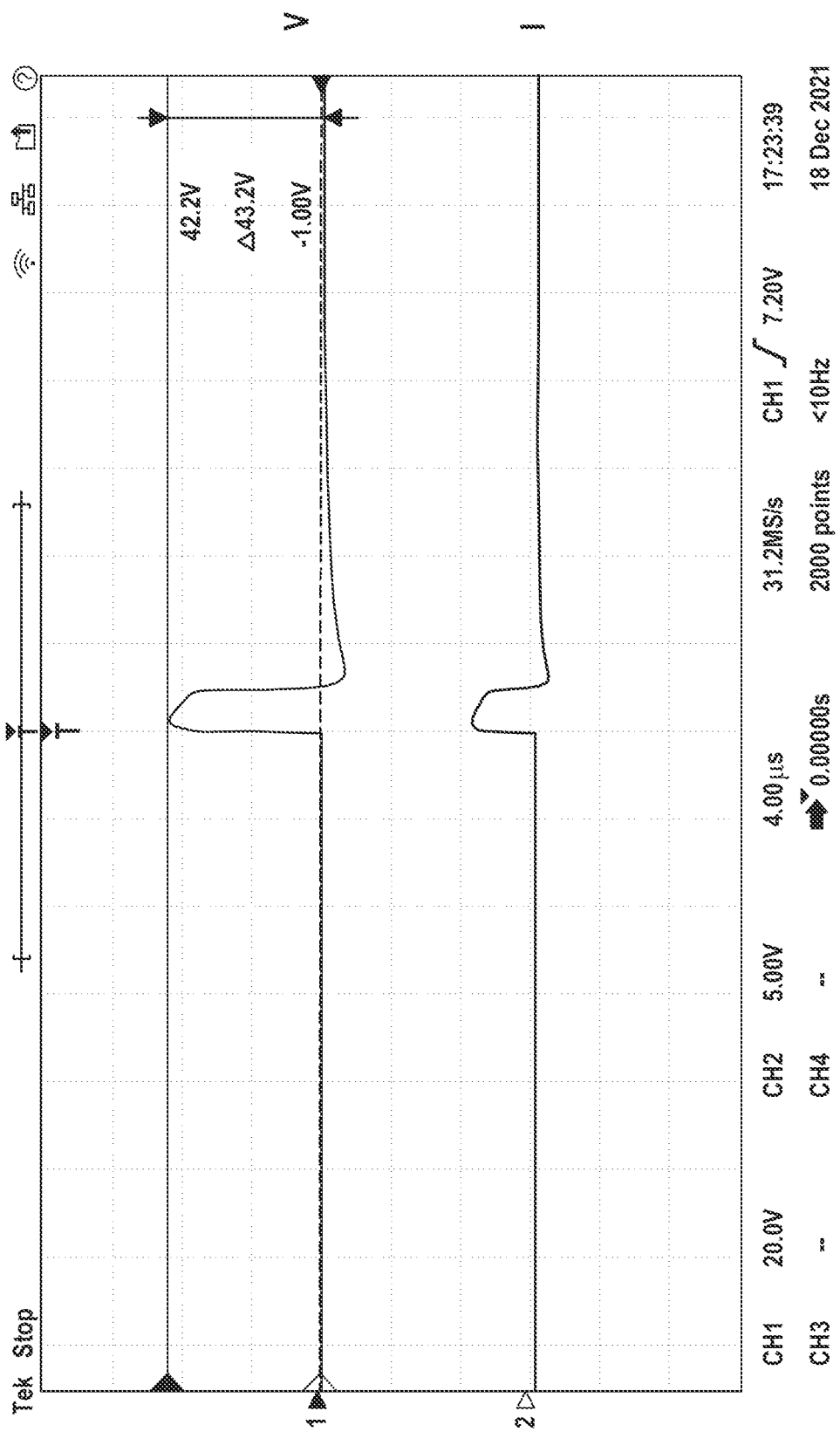
FIG. 6a/b: Representation of a third example of a charge-balanced voltage and current pulse implemented by a generator according to the invention.
Figure 6B:
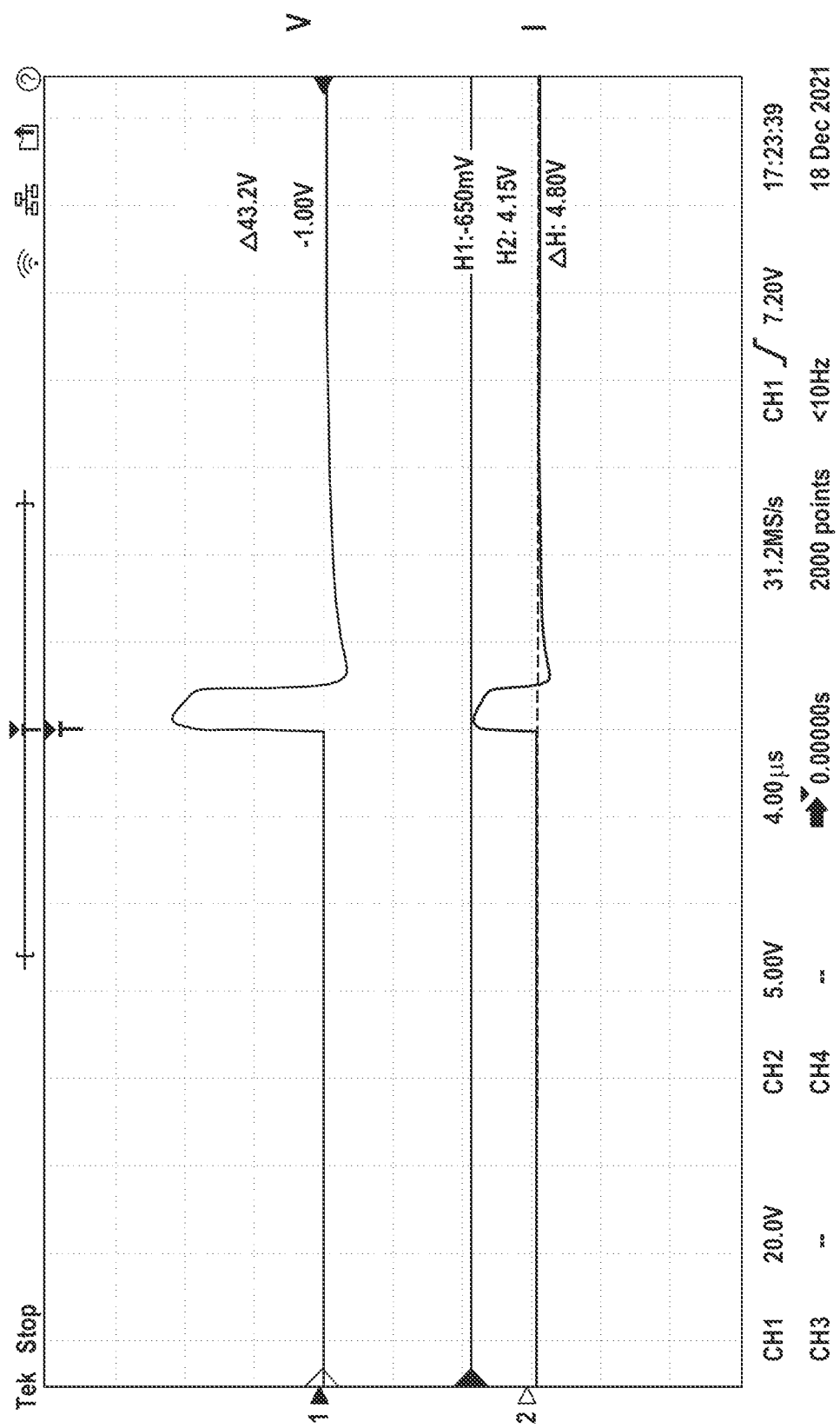

FIG. 6*a/b* shows a representation of a third example of a charge-balanced voltage and current pulse implemented by a generator according to the invention. The channel scaling corresponds to the channel scaling of FIGS. 4*a/b*. In FIG. 6*a/b* the total impedance was determined as 90 Ohm. The total capacitance was set to 0.13 µF. Regarding the voltage characteristics, the amplitude of the voltage pulse in this example may peak at about +4320 V and at about −800 V. Regarding the current characteristics, the amplitude of the current pulse in this example may peak at about +41.5 A and at about −15 A. The exemplary pulse shown on the oscilloscope display may also be used as a suitable PFA waveform for a tissue ablation.

Figure 7:
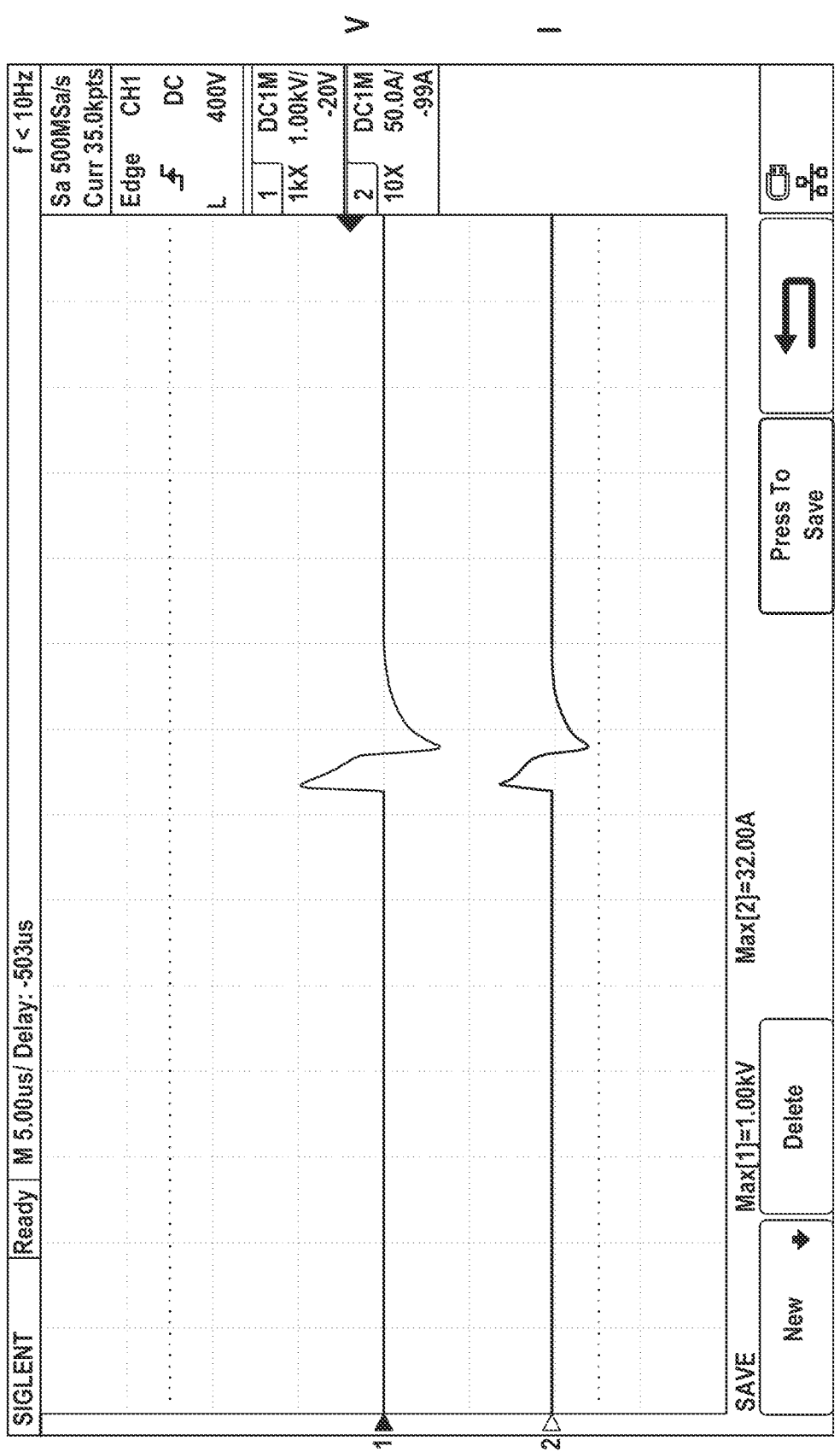
FIG. 7: Representation of a fourth example of a charge-balanced voltage and current pulse implemented by a generator according to the invention.

FIG. 7 shows a representation of a fourth example of a charge-balanced voltage and current pulse implemented by a generator according to the invention. In FIG. 7 the total impedance was determined as 90 Ohm. The total capacitance was set to 0.03 µF. This example may illustrate qualitatively the effect of the chosen total capacitance. The total capacitance is comparatively lower to the total capacitance of the example of FIG. 6*a/b* which, however, comprise the same total impedance. Hence, by adapting the total capacitance the symmetry of the waveform of the substantially charge-balanced pulse may be systematically adjusted.

Figure 8:
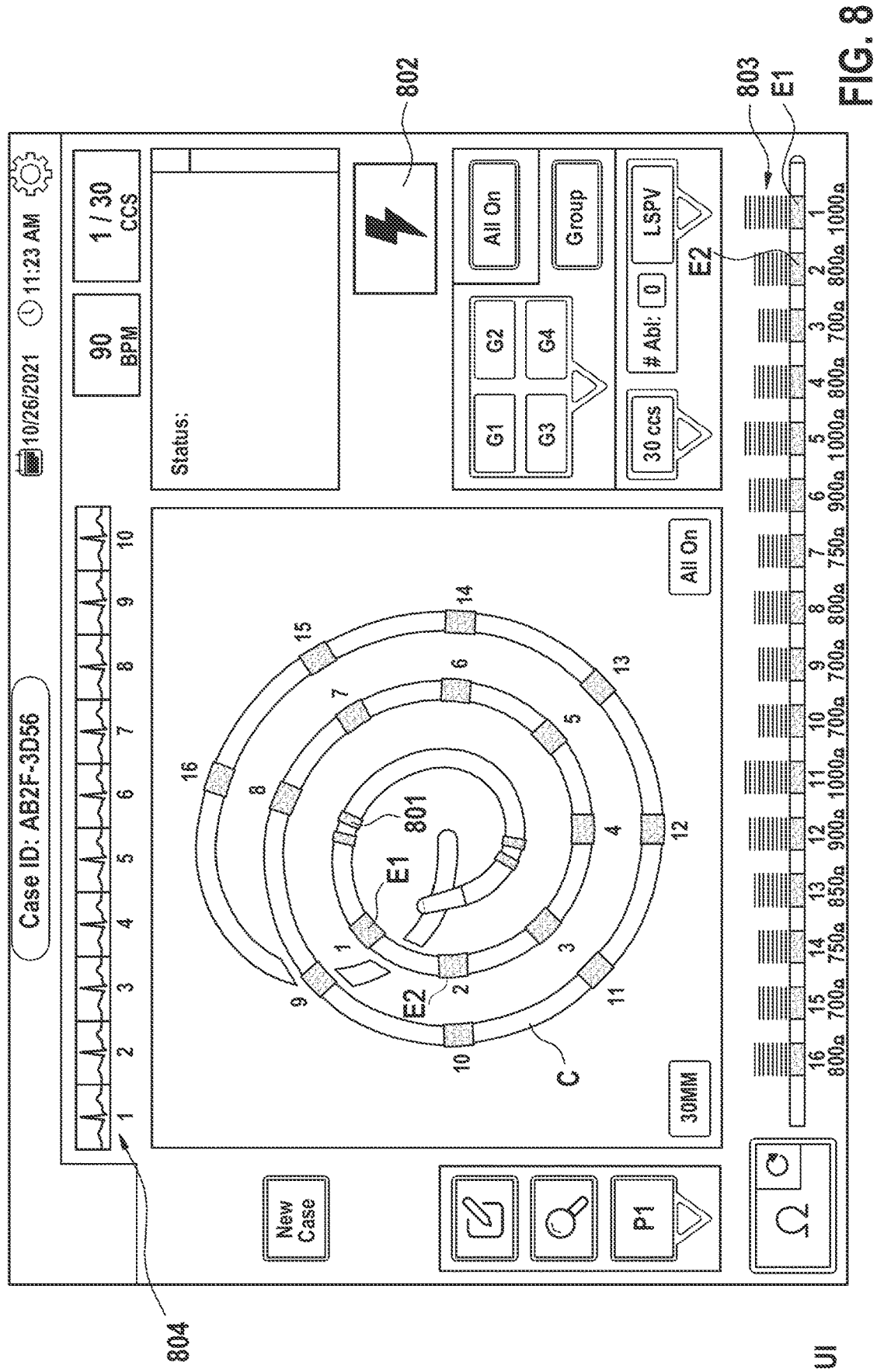
FIG. 8: Representation of an exemplary user interface of a generator according to the invention.

FIG. 8 shows a representation of a user interface UI which may be communicatively coupled to a generator or be part of a generator according to the invention. FIG. 8 may also represent a display of the user interface UI. The user interface UI may be a touchscreen. However, the user interface UI may also be implemented on a monitor wherein an input to the user interface UI may be accomplished via an input device (e.g., a keyboard, a mouse, etc.). The user interface UI may comprise a schematic display of the medical device C. The medical device C in this example may be an ablation catheter. The ablation catheter may comprise various ablation electrodes (e.g., E1, E2), as well as mapping electrodes 801 for sensing and/or mapping purposes (for example, the four lowest electrodes in FIGS. 1 and 2 may correspond to such sensing and/or mapping electrodes). The electrodes of the medical device C may be indicated on the schematic display of the catheter C. The user may select electrodes for active coupling (and thus for a medical treatment) via the user interface. In the example, of FIG. 8 all ablation electrodes were activated for active coupling to the generator. Hence, all electrodes (apart from the purely sensing or mapping electrodes) may be used to facilitate an ablation treatment. The selected electrodes, as well as the number of electrodes may be communicated to the central processing unit CPU. The information may be used, for example, to determine the total impedance (as described herein) and/or the total capacitance to be set in the coupling circuit (as described herein).

At the bottom of the UI, for example, the impedance values for the ablation electrodes of the medical device C may be indicated. For example, the impedance value 803 of the first ablation electrode E1 can be seen in comparison to the other impedance values of the other ablation electrodes. For example, if an electrode impedance is in comparison very high, it may be marked in the user interface UI. High impedances could be attributed to open circuits in the catheter. In such a case the user interface US may not only marks such condition, but the generator may also disallow treatment when a broken electrode is detected this way. In this case the user may have to either disable the broken electrode or exchange the catheter Also, if an electrode impedance is comparatively low, it may also be accordingly marked in the user interface UI. Low impedances could be attributed to electrodes coming close to another or even touching. This would be a possible arcing and/or bubble formation hazard. In such a case the user interface UI may not only marks such condition, but the generator may also disallow treatment when such a short circuit condition is detected. In this case the user may have to either put the close electrodes into different ablation groups or reposition the catheter. Moreover, there may also be a range of impedances defined where treatment is allowed but a warning is presented on the user interface UI that electrodes are close.

The critical impedance threshold (or a critical deviation) may be communicated to the user interface from the generator (e.g., from its central processing unit CPU). Published WO 2022/159665 of the applicant discloses several ways to determine critical impedances. The content of this application is hereby fully incorporated. The user interface may comprise an activation button 802 that may initiate the procedure for applying the substantially charge-balanced pulses via the electrodes. The user interface UI may also indicate an electrocardiogram signal 804 of the patient who may receive the treatment by the medical device C. The user interface UI may also comprise a trigger panel. Upon activation of the trigger panel the trigger time interval with respect to a characteristic cardiac event (e.g., an R wave) may be set. The user interface UI may also comprise an impedance measurement panel. Upon activation of the impedance measurement panel, an impedance measurement may be triggered (e.g., a measurement of the total impedance and/or a measurement of the electrode's impedances). The user interface UI may also comprise a capacitor panel. Upon activation of the capacitor panel, a total capacitance of the capacitor system may be manually set by the user. The activation of the capacitor panel may also trigger the central processing unit CPU to determine an according total capacitance based on the selected electrodes. To that regard, the activation of the capacitor panel may also trigger a measurement of the total impedance. The user interface UI may also comprise an RC time constant panel. Upon activation of the RC time constant panel an RC time constant and/or a range of suitable RC time constants for the coupling circuit may be inputted by the user.

It is noted that the above examples may be combined with further aspects as described herein and details of the examples may also be omitted, as will be understood by the skilled person.

What is claimed is:

1. A generator of a substantially charge-balanced pulse for application to at least one electrode pair of a medical device, the generator comprising:
    a pulse-shaping output stage (POS) for coupling to the at least one electrode pair;
    an internal pulse generator for applying a plurality of internal pulses to the pulse-shaping output stage, the plurality of internal pulses forming a pulse train;
    wherein the pulse-shaping output stage comprises a transformer and at least one capacitor, such that each internal pulse of the pulse train is transformed into a substantially charge-balanced pulse having an interphase period of zero seconds; and
    the pulse-shaping output stage is configured to deliver each charge-balanced pulse of the pulse train to the at least one electrode pair.

2. The generator according to claim 1, wherein the pulse-shaping output stage comprises the capacitor system and the generator is configured such that at least two total capacitances of the capacitor system can be set.

3. The generator according to claim 2, wherein the generator is configured to set the total capacitance of the capacitor system based at least in part on an impedance of the at least one electrode pair.

4. The generator according to claim 2, wherein the generator is configured to set the total capacitance of the capacitor system based at least in part on a number of electrode pairs coupled to the pulse-shaping output stage.

5. The generator according to claim 2, wherein the generator is configured to set the total capacitance of the capacitor system such that a multiplication result of the total capacitance and an impedance of the at least one electrode pair is within a predetermined range.

6. The generator according to claim 1, wherein the pulse-shaping output stage comprises a transformer and a capacitor system, and wherein the generator is further configured such that the internal pulse is coupled from the internal pulse generator to the capacitor system via the transformer.

7. The generator according to claim 1, wherein the generator further comprises:
    means for measuring a voltage and/or a current associated with the at least one electrode pair;
    means for determining an impedance of the at least one electrode pair based on the measurement of the voltage and/or the current.

8. The generator according to claim 1, wherein the internal pulse generator comprises a high-voltage source, wherein the generator is configured to form the internal pulse based at least in part on a high-voltage output of the high-voltage source, wherein the high-voltage source preferably can be set by the generator to provide a high-voltage amplitude of at least 1000 V, preferably at least 1500 V, more preferably at least 2000 V, most preferably at least 3000 V.

9. The generator according to claim 1, wherein the internal pulse generator comprises a switching unit, wherein the switching unit is configured to switch the output of the high-voltage source to generate the internal pulse, wherein the switching unit preferably comprises an H-bridge circuit and/or a half H-bridge circuit.

10. The generator according to claim 9, wherein the internal pulse generator comprises a timing unit for controlling the switching unit preferably to set a timing parameter of the internal pulse and/or to set a number of internal pulses such that a train of internal pulses is applied to the pulse-shaping output stage.

11. The generator according to claim 10, wherein the timing unit is configured to control the switching unit such that the internal pulse is applied based at least in part on a trigger of a medical signal.

12. The generator according to claim 1, wherein the generator is configured to apply a substantially charge-balanced pulse such that, if the at least one electrode pair is placed in the vicinity of human tissue, the substantially charge-balanced pulse causes an irreversible electroporation of a human tissue in the vicinity of the two electrodes.

13. The generator according to claim 1 comprising a user interface configured for receiving and/or displaying the determined impedance of the at least one electrode pair.

14. The generator according to claim 13, whereby the generator is configured for receiving a selection of electrodes via user interface and set the total capacitance based on the selection.

15. The generator according to claim 14, whereby the user interface is configured to display only a selection of electrodes.

16. The generator according to claim 13, whereby the user interface is configured to receive a total capacitance of the capacitor system, RC time constant and/or a range of suitable RC time constants as set by the user.

17. A catheter comprising:
a connector for connecting electrode pairs of the catheter to a generator comprising:
a pulse-shaping output stage (POS) for coupling to the at least one electrode pair;
an internal pulse generator for applying a plurality of internal pulses to the pulse-shaping output stage, the plurality of internal pulses forming a pulse train;
wherein the pulse-shaping output stage comprises a transformer and at least one capacitor, such that each internal pulse of the pulse train is transformed into a substantially charge-balanced pulse having an interphase period of zero seconds; and
the pulse-shaping output stage is configured to deliver each charge-balanced pulse of the pulse train to the at least one electrode pair.

18. The catheter according to claim 17, wherein the pulse-shaping output stage comprises the capacitor system and the generator is configured such that at least two total capacitances of the capacitor system can be set, and wherein the generator is configured to set the total capacitance of the capacitor system based at least in part on an impedance of the at least one electrode pair.

19. The catheter according to claim 17, wherein the pulse-shaping output stage comprises the capacitor system and the generator is configured such that at least two total capacitances of the capacitor system can be set, and wherein the generator is configured to set the total capacitance of the capacitor system based at least in part on a number of electrode pairs coupled to the pulse-shaping output stage.

20. The catheter according to claim 17, wherein the pulse-shaping output stage comprises the capacitor system and the generator is configured such that at least two total capacitances of the capacitor system can be set, and wherein the generator is configured to set the total capacitance of the capacitor system such that a multiplication result of the total capacitance and an impedance of the at least one electrode pair is within a predetermined range.

21. The catheter according to claim 17, wherein the pulse-shaping output stage comprises a transformer and a capacitor system, and wherein the generator is further configured such that the internal pulse is coupled from the internal pulse generator to the capacitor system via the transformer.

22. The catheter according to claim 17, wherein the internal pulse generator comprises a switching unit, wherein the switching unit is configured to switch the output of the high-voltage source to generate the internal pulse, wherein the switching unit preferably comprises an H-bridge circuit and/or a half H-bridge circuit, and wherein the internal pulse generator comprises a timing unit for controlling the switching unit preferably to set a timing parameter of the internal pulse and/or to set a number of internal pulses such that a train of internal pulses is applied to the pulse-shaping output stage, and wherein the timing unit is configured to control the switching unit such that the internal pulse is applied based at least in part on a trigger of a medical signal.

23. A system comprising:
a generator comprising:
a pulse-shaping output stage (POS) for coupling to the at least one electrode pair;
an internal pulse generator for applying a plurality of internal pulses to the pulse-shaping output stage, the plurality of internal pulses forming a pulse train;
wherein the pulse-shaping output stage comprises a transformer and at least one capacitor, such that each internal pulse of the pulse train is transformed into a substantially charge-balanced pulse having an interphase period of zero seconds; and
the pulse-shaping output stage is configured to deliver each charge-balanced pulse of the pulse train to the at least one electrode pair; and
a catheter comprising a connector for connecting electrode pairs of the catheter to the generator.

24. The system according to claim 23, wherein the pulse-shaping output stage comprises the capacitor system and the generator is configured such that at least two total capacitances of the capacitor system can be set, and wherein the generator is configured to set the total capacitance of the capacitor system based at least in part on an impedance of the at least one electrode pair.

25. The system according to claim 23, wherein the pulse-shaping output stage comprises the capacitor system and the generator is configured such that at least two total capacitances of the capacitor system can be set, and wherein the generator is configured to set the total capacitance of the capacitor system based at least in part on a number of electrode pairs coupled to the pulse-shaping output stage.

26. The system according to claim 23, wherein the pulse-shaping output stage comprises the capacitor system and the generator is configured such that at least two total capacitances of the capacitor system can be set, and wherein the generator is configured to set the total capacitance of the capacitor system such that a multiplication result of the total capacitance and an impedance of the at least one electrode pair is within a predetermined range.

27. The system according to claim 23, wherein the pulse-shaping output stage comprises a transformer and a capacitor system, and wherein the generator is further configured such that the internal pulse is coupled from the internal pulse generator to the capacitor system via the transformer.

28. The system according to claim 23, wherein the internal pulse generator comprises a switching unit, wherein the switching unit is configured to switch the output of the high-voltage source to generate the internal pulse, wherein the switching unit preferably comprises an H-bridge circuit and/or a half H-bridge circuit, and wherein the internal pulse generator comprises a timing unit for controlling the switching unit preferably to set a timing parameter of the internal pulse and/or to set a number of internal pulses such that a train of internal pulses is applied to the pulse-shaping output stage, and wherein the timing unit is configured to control the switching unit such that the internal pulse is applied based at least in part on a trigger of a medical signal.

29. A method for generating a substantially charge-balanced pulse for application onto at least one electrode pair of a medical device, comprising:

coupling the at least one electrode pair to a pulse-shaping output stage of a generator comprising:

a pulse-shaping output stage (POS) for coupling to the at least one electrode pair;

an internal pulse generator for applying a plurality of internal pulses to the pulse-shaping output stage, the plurality of internal pulses forming a pulse train;

wherein the pulse-shaping output stage comprises a transformer and at least one capacitor, such that each internal pulse of the pulse train is automatically transformed into a substantially charge-balanced pulse having an interphase period of zero seconds; and the pulse-shaping output stage is configured to deliver each charge-balanced pulse of the pulse train to the at least one electrode pair; and applying a predetermined internal pulse with the internal pulse generator of the generator to generate a substantially charge-balanced pulse in the at least one electrode pair.

30. The method according to claim 1, further comprising:

measuring a voltage and/or a current associated with the at least one electrode pair; and determining an impedance of the at least one electrode pair based on the measurement of the voltage and/or the current.

* * * * *